US011039803B1

(12) United States Patent
Butani et al.

(10) Patent No.: US 11,039,803 B1
(45) Date of Patent: Jun. 22, 2021

(54) SYSTEM AND METHOD FOR CABINET RADIOGRAPHY INCORPORATING A GAMMA OR OTHER PROBE

(71) Applicant: KUB Technologies Inc., Stratford, CT (US)

(72) Inventors: Vikram Butani, Stratford, CT (US); Chester Lowe, Stratford, CT (US); Vignesh Mandalapa-Bhoopathy, Stratford, CT (US); Edwin Maria-Selvaraj, Stratford, CT (US); John Pizzonia, Stratford, CT (US); Peter Yasutake, Stratford, CT (US)

(73) Assignee: Kub Technologies, Inc., Stratford, CT (US)

( * ) Notice: Subject to any disclaimer, the term of this patent is extended or adjusted under 35 U.S.C. 154(b) by 0 days.

(21) Appl. No.: 17/036,085

(22) Filed: Sep. 29, 2020

Related U.S. Application Data

(60) Provisional application No. 63/019,235, filed on May 1, 2020.

(51) Int. Cl.
*A61B 6/00* (2006.01)
*A61B 6/02* (2006.01)

(52) U.S. Cl.
CPC ............. *A61B 6/502* (2013.01); *A61B 6/025* (2013.01); *A61B 6/4258* (2013.01); *A61B 6/4417* (2013.01); *A61B 6/461* (2013.01); *A61B 6/508* (2013.01)

(58) Field of Classification Search
CPC .............................. A61B 6/025; G01N 23/044
See application file for complete search history.

(56) References Cited

U.S. PATENT DOCUMENTS

| 9,138,193 | B2 | 9/2015 | Lowe et al. |
| 10,492,747 | B2 | 12/2019 | Divakaran et al. |
| 10,670,545 | B2 | 6/2020 | Butani et al. |
| 10,729,399 | B2 * | 8/2020 | Butani .................. A61B 6/025 |

* cited by examiner

*Primary Examiner* — Dani Fox
(74) *Attorney, Agent, or Firm* — Ziegler IP Law Group, LLC

(57) ABSTRACT

It would be advantageous with the close quarters in breast procedure rooms to create a system and method incorporating 2 modalities utilized in breast intervention procedures for the diagnosis and verification for breast cancer. Systems for specimen radiography assist radiologists and surgeons in the detection and classification of abnormal lesions in medical images gleaned from breast biopsies/lumpectomies and a Gamma or other probe system with a sensor to detect radioactive, metallic/magnet, or RFID waves to help locate a lump or abnormality which were placed by an Interventional Radiologist. With the utilization of a dual modality machine, the physician can detect the abnormalities, remove the abnormalities, and verify that they have achieved a clean margin, currently 1 mm, from the cancerous or abnormal tissues. Currently it is believed that there is not a system or method utilizing both a Gamma or other probe and Radiography in a cabinet system.

20 Claims, 13 Drawing Sheets

FRONT VIEW INTO CABINET
Door Open

Typical Example of an X-ray Cabinet System

View in Sample Chamber with Door Open with
X-ray source at position (14) Top Center

**Lateral View of X-Ray Source
Mounted to Swing Arm at position (14)

SYSTEM AND METHOD FOR CABINET RADIOGRAPHY INCORPORATING A GAMMA OR OTHER PROBE

CROSS-REFERENCE TO RELATED APPLICATIONS

This application claims priority to and the benefit of U.S. Provisional Patent Application Ser. No. 63/019,235 filed May 1, 2020, the disclosure of which is incorporated herein by reference in its entirety.

BACKGROUND

Field of the Present Disclosure

The present disclosure relates to the field of a cabinet x-ray incorporating both radiography and wired and wireless Gamma Probe or other probe device facilitating the detection of implanted sources whether they be RFID, metallic/magnetic, or radioactive and for the production of radiographic organic and non-organic images.

Background

It would be advantageous in breast procedures due to the close proximity of instruments and furniture present in an operating room theater to create a system and method incorporating the 2 main modalities utilized in breast biopsies and surgeries for the diagnosis and verification for breast cancer. Systems for specimen analysis having dual modality can include radiography apparatus to assist radiologists and surgeons in the detection and classification of abnormal lesions in medical images gleaned from breast biopsies/lumpectomies and a probe system utilized to detect implanted seed markers, whether they are radioactive, magnetic, or RFID, to help the surgeon locate or delineate a lump or abnormality and facilitate the removal of a suspect tissue sample.

A Gamma Probe is a handheld device used with a Geiger-Muller tube or scintillation counter, for intraoperative use following interstitial injection of a radionuclide, to locate regional lymph nodes by their radioactivity. It is used primarily for sentinel lymph node mapping and parathyroid surgery. The Gamma Probe is also used for RSL (Radioactive Seed Localization), to locate small and non-palpable breast lesions. The output of a gamma probe is a series of pulses, which are counted for a predetermined amount of time.

With the utilization of a dual modality machine, the physician can use either modality to detect the abnormalities, remove the abnormalities, and verify that they have achieved a clean margin, currently 1 mm, from the cancerous or abnormal tissues.

Currently it is believed that there is not a system or method utilizing both a Gamma or other probe and Radiography in a cabinet system.

Today, conventional breast specimen systems can gather a digital breast specimen radiogram separately. In these systems, the radiograms of a woman's breast specimen are viewed separately for detecting suspicious lesions. Suspicious lesions are located on each image.

With a dual modality unit, the physician can utilize the Gamma or other probe system and immediately locate preplaced seeds in the breast before excision as well as the excised tissue and utilize sound (e.g., an audible signal including, for example, a series of beeps that get closer together as the detected material is closer in proximity to the probe) and an analog signal display to locate the radio-opaque clip inside the cancerous tissue saving time for both the patient on the treatment table and the physician, thereby reducing cost while improving quality of care.

Breast cancer is the most common cancer among women other than skin cancer and is the second leading cause of cancer death in women after lung cancer. The American Cancer Society currently estimates that there are about 182,460 new cases of invasive breast cancer per year among women in the United States and 40,480 deaths per year from the disease. Prevention and early diagnosis of breast cancer are of foremost importance. Because early breast cancer does not produce symptoms, the American Cancer Society recommends an x-ray radiogram screening and a clinical breast examination every year for women over the age of 40. Recently, the American Cancer Society has additionally recommended an adjunctive breast MRI (magnetic resonance imaging) screening for women in certain higher-risk groups. Although the preferred embodiments described herein below are particularly applicable and advantageous for use in x-ray mammography and x-ray tomosynthesis breast cancer screening environments, they are also readily applicable for other breast imaging modalities such as breast specimen radiography and digital breast specimen tomosynthesis.

Lumps or abnormalities in the breast are often detected by physical examination, mammography, ultrasound, or other imaging studies. However, it is not always possible to tell from these imaging tests whether a growth is benign or cancerous.

A breast biopsy is performed to remove some cells from a suspicious area in the breast and examine them under a microscope to determine a diagnosis. This can be performed surgically or, more commonly, by a radiologist using interventional radiography to implant seeds denoting the orientation and location of the suspected lesions and/or masses.

In seed guided breast biopsy, a Gamma or other probe can be used to help guide the radiologist's instruments to the site of the abnormal growth.

A seed guided breast biopsy can be performed when a breast ultrasound or mammogram shows an abnormality such as:
a suspicious solid mass
a distortion in the structure of the breast tissue
an area of abnormal tissue change There are times when a physician may decide that a Gamma or other probe included in the present disclosure may be utilized to locate implanted seeds even for a mass that can be felt.

The Gamma Probe system consists of a console containing a computer and electronics, a video display screen, a speaker, and a transducer/detector that is used to do the scanning. The probe is a small handheld device that resembles a small pipe with a bigger cylindrical handle on one end, attached to the scanner by a cord or in this particular embodiment via Bluetooth. The detector of the probes of the present disclosure sense radioactivity, magnetic metal, or RFID (radio frequency identification) signals emitted by implanted seeds and sends a signal to the base unit on the strength of the detected signal creating a sound and a display on an analog screen informing the operator the locality of the seed from the tissues in the body. The principles are similar to a Geiger counter/sensor.

The sound and analog signal on a graph or dial is created based on the amplitude (loudness), frequency (pitch) and time it takes for the signal to be sensed from the area within the patient that is being examined to the Gamma or other probe (the device used to examine the patient), as well as the type of body structure and composition of body tissue through which the radioactivity, magnetism, or RFID travels.

The sentinel node market experienced high growth in the early and mid 90's starting with melanoma sentinel node surgical search and breast cancer sentinel node staging; both are currently considered standards of care. Most surgeons propose node staging after a positive breast biopsy. New applications are being developed for parathyroid direct detection and intra-operative detection of cancerous tissue using tumor-seeking radiopharmaceuticals. Parathyroid detection is growing fast, while the intraoperative use of gamma or other probes for direct tumor detection is just emerging.

Isotopes for clinical use with Gamma Probes can include the following:
Tc99m—Technetium-99m
I125—Iodine 125
I131—Iodine 131
In111—Indium 111
F18—Fluorine 18
Ga68—Gallium 68

Specimen Radiography is considered the most cost-effective screening method for the detection of breast cancer in surgically removed breast tissue. However, the sensitivity of specimen radiography is often limited by the presence of overlapping dense fibroglandular tissue in the breast specimen. Dense parenchyma reduces the conspicuity of abnormalities and thus constitutes one of the main causes of missed breast cancer diagnosis.

Digital breast specimen tomosynthesis as exhibited in U.S. Pat. No. 2015/0131773 (U.S. Pat. No. 9,138,193), Lowe, et al., entitled "SPECIMEN RADIOGRAPHY WITH TOMOSYNTHESIS IN A CABINET," the disclosure of which is hereby incorporated by reference in its entirety in the present application, with the incorporation a promising method that may help reduce the camouflaging effects of dense breast tissue and improve the sensitivity of specimen radiography for breast cancer detection in dense breasts.

A preferred embodiment system would incorporate both the Digital Breast Specimen Cabinet and Gamma Probe systems in 1 unit.

SUMMARY

The present disclosure relates to the field of a cabinet x-ray incorporating both radiography and wired and wireless Gamma or other probes facilitating the detection of implanted sources whether they be RFID, metallic objects that are magnetic, or radioactive material and for the production of radiographic organic and non-organic images. In particular, the present disclosure relates to a method and apparatus for creating and utilizing a dual modality unit in the assistance for allowing more sensitive and reliable identification of suspicious, i.e., possibly cancerous, lesions in the case of breast specimens and the verification of the interventional procedures.

An embodiment of the present disclosure includes a cabinet x-ray system incorporating a Gamma or other probe device, including a cabinet x-ray system, a base unit including an image processor and a display, and a gamma or other probe operably connected to the base unit. The probe includes a head portion including a sensor; a plurality of receiver modules; a processing unit that controls the receiver modules and the analog-to-digital converter, the receiver modules causing the Gamma or other probe to receive data until the target object is scanned; and an interface for enabling the digital signal to be transferred from the Gamma or other probe to the image processor of the base unit. The probe can further comprise a sensor that actuates to create analog signals which are amplified by the base unit to create an audible sound. The probe can include a battery for providing power to components of the probe. The interface can be a wireless interface, and wherein the base unit includes a wireless interface. The wireless interface of the probe and the base unit communicate can be via a wireless data transfer protocol. The interface can include a cable interface between the probe and the base unit. The sensor can produce a differential output of amplified analog signals. base unit can be a computer. The sensor can attenuate to a radioactive seed or radioisotope. The sensor can attenuate to a RFID transmitter. The sensor cab attenuates to a metallic or magnetic seed.

In one embodiment, a cabinet x-ray and gamma probe system for obtaining x-ray images and gamma probe measurements of a specimen is provided. The system includes a cabinet defining an interior chamber, a first display, an x-ray system, a controller and a gamma probe system. The x-ray system includes an x-ray source, an x-ray detector and a specimen platform. The controller is configured to selectively energize the x-ray source to emit x-rays through the specimen to the x-ray detector; control the x-ray detector to collect a projection x-ray image of the specimen when the x-ray source is energized; and selectively display the x-ray image on the display. The gamma probe system includes a gamma probe configured to receive external radiated signals from external sources and transmit electronic signals corresponding to the external radiated signals received to the gamma probe base unit; and a gamma probe base unit in communication with the gamma probe and including a processor, the processor configured to receive the electronic signals received from the gamma probe and present the electronic signals as at least one of a visual numerical readout on the first display, a visual numerical readout on a second display and generate a sound output.

In another embodiment, a cabinet x-ray, optical camera and gamma probe system for obtaining x-ray images, projection x-ray images, reconstructed tomosynthetic x-ray images, optical images and gamma probe measurements of a specimen is provided. The system includes a cabinet defining an interior chamber and an equipment enclosure, a display, an x-ray system, a gamma probe system, an optical camera and a controller. The x-ray system includes an x-ray source positioned in the interior chamber; an x-ray detector positioned in the interior chamber; a specimen platform positioned in the interior chamber configured to have the specimen positioned thereon and which is a protective cover of and in physical contact with the x-ray detector; and a motion control mechanism positioned in the interior chamber and configured for moving the x-ray source to or along a plurality of positions within the interior chamber relative to the specimen disposed on the specimen platform. The gamma probe system includes a gamma probe configured to receive external radiated signals from external sources and transmit electronic signals corresponding to the external radiated signals received to the gamma probe base unit; and a gamma probe base unit in communication with the gamma probe and including a processor, the processor configured to receive the electronic signals received from the gamma probe and send the electronic signals to a controller. The optical camera is configured to capture an optical image of the interior chamber. The controller is positioned in the equipment enclosure and configured to selectively energize the x-ray source to emit x-rays through the specimen to the x-ray detector at selected positions of the x-ray source relative to the specimen such that the isocenter of the emitted x-rays at the selected positions is located at a surface of the x-ray detector; control the x-ray detector to collect a projection x-ray images of the specimen when the x-ray source is energized at the selected positions, wherein one of the projection x-ray images is a two-dimensional x-ray image taken at standard imaging angle of approximately 0°; create a tomosynthetic x-ray image reconstructed from a collection of projection x-ray images; process the collection of the projection x-ray images in the controller into one or more reconstructed tomosynthetic x-ray images representing a volume of the specimen and relating to one or more image planes that are selectively the same or different from that of the two-dimensional x-ray image; store the projection x-ray images and the one or more reconstructed tomosynthetic x-ray images; control the optical camera to capture and collect the optical image of the specimen and the gamma probe in the interior chamber; selectively display a superimposed image comprising a first image including the optical image in real time superimposed on top of a second image of the two-dimensional x-ray image or one of the reconstructed tomosynthetic x-ray images such that when the gamma probe is present in the interior chamber, the gamma probe and its movement relative to the specimen in the first superimposed image are displayed on the display; selectively change the opacity of the first image of the first superimposed image to form a second superimposed image; and selectively display the second superimposed image such that when the gamma probe is present in the interior chamber, the gamma probe and its movement relative to the specimen in the second superimposed image are displayed on the display.

In another embodiment is a method for obtaining an x-ray image and gamma probe measurements of a specimen in a cabinet x-ray and gamma probe system, processing and displaying the x-ray image and gamma probe system measurements of the specimen is provided. The cabinet x-ray and gamma probe system includes a cabinet defining an interior chamber, a first display, an x-ray system, a gamma probe system and a controller. The x-ray system includes an x-ray source; an x-ray detector; and a specimen platform. The controller is configured to selectively energize the x-ray source to emit x-rays through the specimen to the x-ray detector; control the x-ray detector to collect a projection x-ray image of the specimen when the x-ray source is energized; and selectively display the x-ray image on the display. The gamma probe system includes a gamma probe configured to receive external radiated signals from the specimen and transmit electronic signals corresponding to the external radiated signals received to the gamma probe base unit; and a gamma probe base unit in communication with the gamma probe and including a processor, the processor configured to receive the electronic signals received from the gamma probe and present the electronic signals as at least one of a visual numerical readout on the first display, a visual numerical readout on a second display and generate a sound output. The method includes controlling the x-ray detector to collect an x-ray image of the specimen when the x-ray source is energized; controlling the gamma probe to receive the external radiated signals from the specimen and transmit the electronic signals corresponding to the external radiated signals received to the gamma probe base unit; selectively displaying at least one of the x-ray image on the display; and selectively presenting the electronic signals received by the gamma probe base unit as at least one of a visual numerical readout on the first display, a visual numerical readout on a second display and generate a sound output.

BRIEF DESCRIPTION OF THE DRAWINGS

To further clarify the above and other advantages and features of the present disclosure, a more particular description of the present disclosure will be rendered by reference to specific embodiments thereof that are illustrated in the appended drawings. It is appreciated that these drawings depict only typical embodiments of the present disclosure and are therefore not to be considered limiting of its scope. The present disclosure will be described and explained with additional specificity and detail through the use of the accompanying drawings in which.

DETAILED DESCRIPTION OF EMBODIMENT

Figure 1:
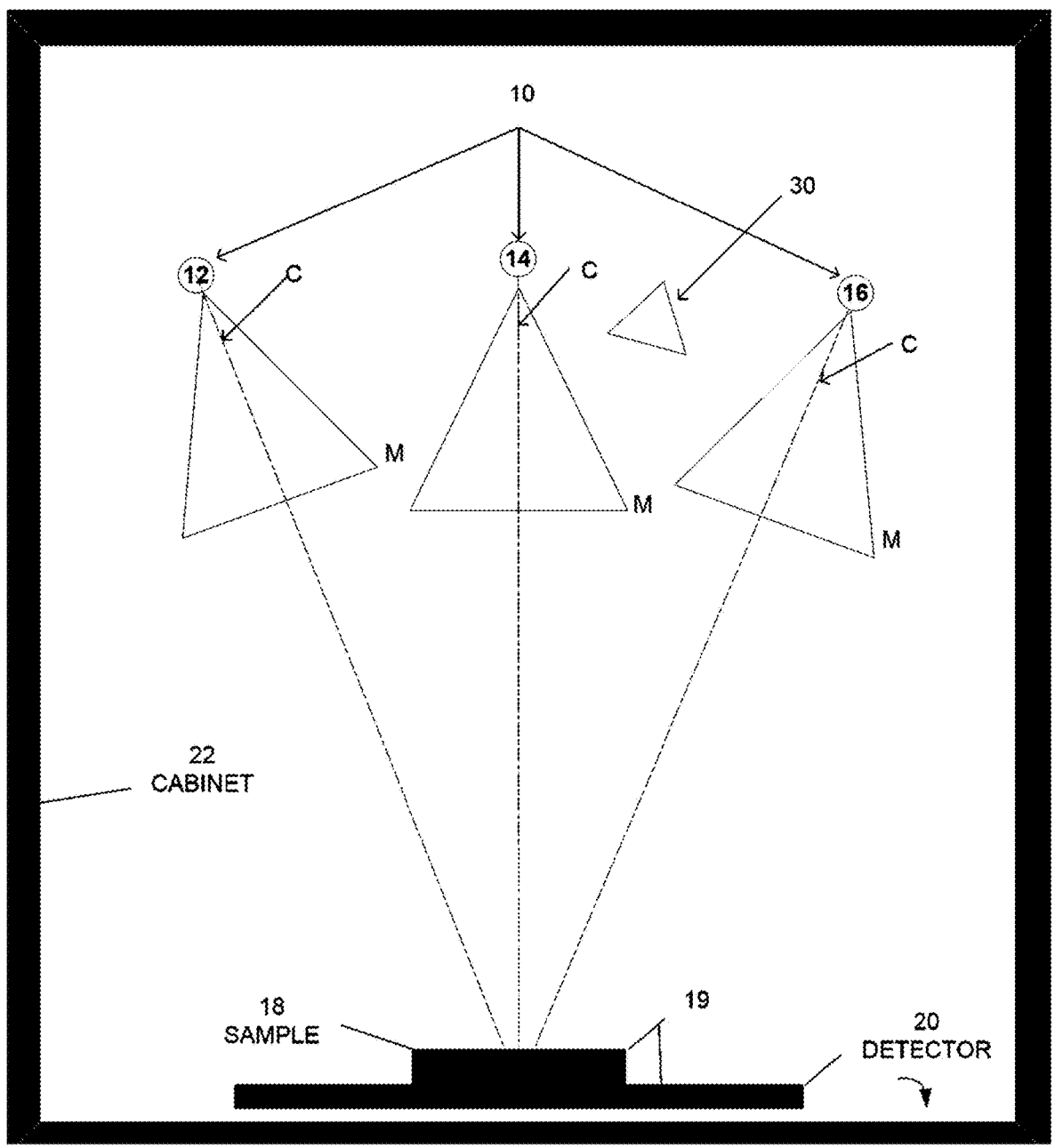
FIG. 1—Schematically illustrates a front view of an x-ray source, a specimen/sample, and a digital detector, where the x-ray source moves relative to the specimen for imaging the specimen at different angles, in one embodiment of a system incorporating aspects of the present disclosure.

In general, aspects of this disclosure include a device (cabinet x-ray system) utilizing a camera to capture an optical image (in black and white, gray scale or color, preferably color), preferably in real-time, of a sample or specimen and/or x-rayed to produce an x-ray image of the sample or specimen and utilizing a probe system, for example, a gamma or other probe system, that is incorporated into the device or separate therefrom to locate to detect different substances, tags or implants as well as anatomical features that can be detected as disclosed herein. The x-ray image can include a two-dimensional (2-D) x-ray image or a synthetic x-ray image assembled from more than one x-ray image (e.g., a tomosynthetic image).

In particular, the present disclosure includes a method and apparatus for creating and utilizing a dual modality unit (probe data and x-ray data including images or camera data including images) or a triple modality unit ((probe data and x-ray data including images and camera data including images) in the assistance for allowing more sensitive and reliable identification of suspicious, i.e., possibly cancerous, lesions in the case of breast specimens and the verification of the interventional procedures.

A probe for use in the detection of implant applications is disclosed. In one embodiment, the probe comprises a base unit that includes interpretation unit and a receptor for the signal from the probe. The probe is operably connected to the base unit via wirelessly (e.g., Bluetooth) or direct wiring. The probes of the present disclosure includes a head portion including a sensor array that may detect a radioactive source (e.g., a gamma probe), metallic objects (if they are magnetic objects), or a RFID implant that emits a radio frequency signal. A plurality of receiver modules that cause the probe to detect different substances is also included in the probe. An interface is included for enabling the signal to be transmitted from the probe to the base unit either wirelessly (e.g., Bluetooth) or direct wiring. In particular, the present disclosure relates to a method and apparatus for creating and utilizing a dual modality unit or a triple modality unit in the assistance for allowing more sensitive and reliable identification of suspicious, i.e., possibly cancerous, lesions in the case of breast specimens and the verification of the interventional procedures.

Embodiments of the present disclosure include embodiments disclosed herein that include a gamma probe as well as embodiments disclosed herein that include a probe that detect radioactivity, metallic objects (if they are magnetic objects), or a RFID implant that emits a radio frequency signal in place of the gamma probe or in addition to it.

The probe and data obtained therefrom can be used along with a photo/captured camera optical image, preferably in real-time, that may be displayed on the monitor or the resultant x-ray image or synthetic x-ray image assembled from more than one x-ray image (e.g., a tomosynthetic image) of the sample separately or as back to back viewing or where the camera and x-ray images are overlaid onto one another for example, as a side-by-side or Picture-In-a-Picture (PIP) image of the sample. A device capturing both an x-ray image and an optical image, the latter two preferably in real-time, of the specimen facilitates confirmation and orientation for the clinician to verify margins and other specimen features are achieved by the professional after it is removed from a patient.

A preferred embodiment system would be to incorporate an HD (high-definition) optical camera into a cabinet x-ray unit allowing the system to capture an HD optical image and x-ray image of the specimen along with the probe system of the present disclosure, although an embodiment is also disclosed herein including the probe system of the present disclosure with a cabinet x-ray unit which can capture an HD optical image or an x-ray image of the specimen.

The present disclosure and embodiments included therein can relate to specimen radiography but the disclosure is not isolated to specimen radiography but may be utilized, for example, for non-destructive testing, pathology as well as any radiographic analysis of organic and non-organic samples or specimens, requiring a cabinet x-ray system but is not limited to just an HD camera but to any camera fitting within the confines of the cabinet x-ray system as well as probe system of the present disclosure.

Reference will now be made to figures wherein like structures will be provided with like reference designations. It is understood that the drawings are diagrammatic and schematic representations of exemplary embodiments of the disclosure and are not limiting of the present disclosure nor are they necessarily drawn to scale. FIGS. 1-11 depict various features and uses of embodiments of the present disclosure, which embodiments are generally directed to a system that can utilize an optical camera, preferably an HD or similar real-time camera, to capture an image of the specimen/sample concurrently with the acquisition of an x-ray image.

The systems and methods of embodiments of the present disclosure also address unmet needs by providing 2-D x-ray imaging and tomosynthesis apparatus and techniques that include optical imaging for imaging breast specimens that overcome the shortfall of the data received from two-dimensional and tomosynthesis imaging systems alone. The aspects of embodiments of the present disclosure also enable the use of tomosynthesis to efficiently provide accurate three-dimensional imaging of a specimen in which overlapping images having differing attenuation characteristics can be obtained by applying a three-dimensional reconstruction algorithm all in an x-ray cabinet system.

As used herein, the term "computer," "computer system", or "processor" refers to any suitable device operable to accept input, process the input according to predefined rules, and produce output, including, for example, a server, workstation, personal computer, network computer, wireless telephone, personal digital assistant, one or more microprocessors within these or other devices, or any other suitable processing device with accessible memory.

The term "computer program" or "software" refers to any non-transitory machine-readable instructions, program or library of routines capable of executing on a computer or computer system including computer readable program code.

Digital breast specimen tomosynthesis is disclosed in U.S. Patent Publication No. 2015/0131773 (granted as U.S. Pat. No. 9,138,193), Lowe, et al., entitled "SPECIMEN RADIOGRAPHY WITH TOMOSYNTHESIS IN A CABINET" as it relates to the present subject matter of the title and related disclosure; U.S. Pat. No. 10,670,545, entitled "SYSTEM AND METHOD FOR CABINET X-RAY SYSTEMS WITH CAMERA" as it relates to the present subject matter of the title and related disclosure; U.S. Pat. No. 10,729,399, entitled "SYSTEM AND METHOD FOR CABINET X-RAY SYSTEM WITH CAMERA AND X-RAY IMAGES SUPERIMPOSITION" as it relates to the present subject matter of the title and related disclosure; and U.S. Pat. No. 10,492,747, entitled "SYSTEM AND METHOD FOR EXTENDING AND RETRACTING A MOVEABLE ARM" as it relates to the present subject matter of the title and related disclosure, the disclosures of which are hereby incorporated by reference in their entirety.

The terms "camera" or "optical camera" refer to an instrument, including an optical instrument for capturing images in black and white, gray scale or color (preferably color) using reflected and/or emitted wavelengths of the electromagnetic spectrum, for example, visible light or fluorescent light, from an object, similar to a photograph or that which could be viewed by a human eye, using an electronic light-sensitive sensor array. These terms may include such instruments producing images in standard resolution or HD as well as a digital camera that can directly capture and store an image in computer-readable form using an array of electronic light-sensitive elements—typically semiconductor photo-sensors—that produce a light-intensity-dependent electronic signal in response to being illuminated.

Reference will now be made to figures wherein like structures will be provided with like reference designations. It is understood that the drawings are diagrammatic and schematic representations of exemplary embodiments of the disclosure and are not limiting of the present disclosure nor are they necessarily drawn to scale.

Specimen tomography is a three-dimensional specimen imaging system. It involves acquiring images of a sample at multiple viewpoints, typically over an arc or linear path. The three-dimensional image is constructed by the reconstruction of the multiple image data set.

One embodiment of a system 100 incorporating aspects of the present disclosure is illustrated in FIG. 1 The system 100 is totally enclosed or housed in an X-ray cabinet 22. In accordance with the aspects of the disclosed embodiments, the X-ray source 10 moves around the stationary sample, 18, typically, but not necessarily, in an arc. References 12, 14, and 16 of FIG. 1 illustrate exemplary positions of the X-ray source 10 within the X-ray cabinet 22. The reference "C" at each of the positions 12, 14, 16 of the X-ray source 10 in FIG. 1 refers to the point source of the X-ray beam. The reference "M" refers to the spread or fan of the X-ray beam.

While the x-ray detector 20 (which can include a digital x-ray detector, a flat x-ray detector and a flat digital x-ray detector) may move or rotate, in accordance with one aspect of the present disclosure, the x-ray detector 20 remains stationary relative to the sample 18 and X-ray source 10 to maintain an equidistant center point. The X-ray data taken at each of a number of exemplary positions 12, 14, 16 of the X-ray source 10 relative to the sample 18 within the X-ray cabinet 22 is processed to form images, where two or more of the differing image positions are utilized to form a digital tomosynthesis image.

In one embodiment, the aspects of the present disclosure limit the arc or linear travel of the x-ray source 10 over about a 20° to about a 50° arc, preferable about 30°, more preferable 20°. The movement can be clockwise or counter clockwise along a path, which includes for example, one or more, or a combination thereof, of the following exemplary ranges: between approximately 350° (reference position 12) to 0° (reference position 14) to 10° (reference position 16), or between approximately 340° (reference position 12) to 0° (reference position 14) to 20° (reference position 16) and or between approximately 335° (reference position 12) to 0° (reference position 14) to 25° (reference position 16). The ranges recited herein are intended to be approximate and inclusive of start and endpoints. In the example of FIG. 1 the x-ray detector 20 is stationary as is the sample 18. The sample 18 also referred to as the "object" or "imaging object" is disposed on or rests on the specimen platform 19 (which is a protective cover) or other surface of the x-ray detector 20.

In operation, source 10 is energized to emit an x-ray beam, generally throughout its travel along one or more of the paths or positions described above. The x-ray beam travels through the sample 18 to the x-ray detector 20 and the multiple images collected at varying angles are stored and then utilized for the tomosynthesis reconstruction. The X-ray source 10 may range from about 0 kVp to about 90 kVp, preferably a 50 kVp 1000 μa X-ray source.

Different embodiments of the present disclosure can utilize different ranges of motion of one or more of the X-ray source 10 and x-ray detector 20 as well as changing the angularity of one or both. The aspects of the present disclosure differ from previous systems either the x-ray detector 20 and x-ray source 10 and/or the isocenter is above the sample and the isocenter is not at the detector surface. The isocenter of embodiments of the present disclosure is preferably positioned at the detector surface, for example, as shown in FIG. 1 where the reference "C" all converge for each of the positions 12, 14, 16 of the X-ray source 10 in FIG. 1. In accordance with the aspects of the present disclosure, in one embodiment, the X-ray source 10 is configured to move, as described herein, while the detector is configured to remain stationary or in a fixed position.

The detector 20 and associated electronics generate image data in digital form for each pixel at each of the angular positions, 12, 14, 16 of X-ray source 10 and translations positions of the detector 20 relative to the sample 18. While only three positions 12, 14, 16 are illustrated in FIG. 1, in practice more images are taken at differing angles. For example, in one embodiment, images can be taken at approximately every 1° of rotation or motion of source 10. The camera 30 represented in the figure may capture an optical image, preferably an HD image of the sample which can be stored with the radiographic images in computer 470.

Figure 2:
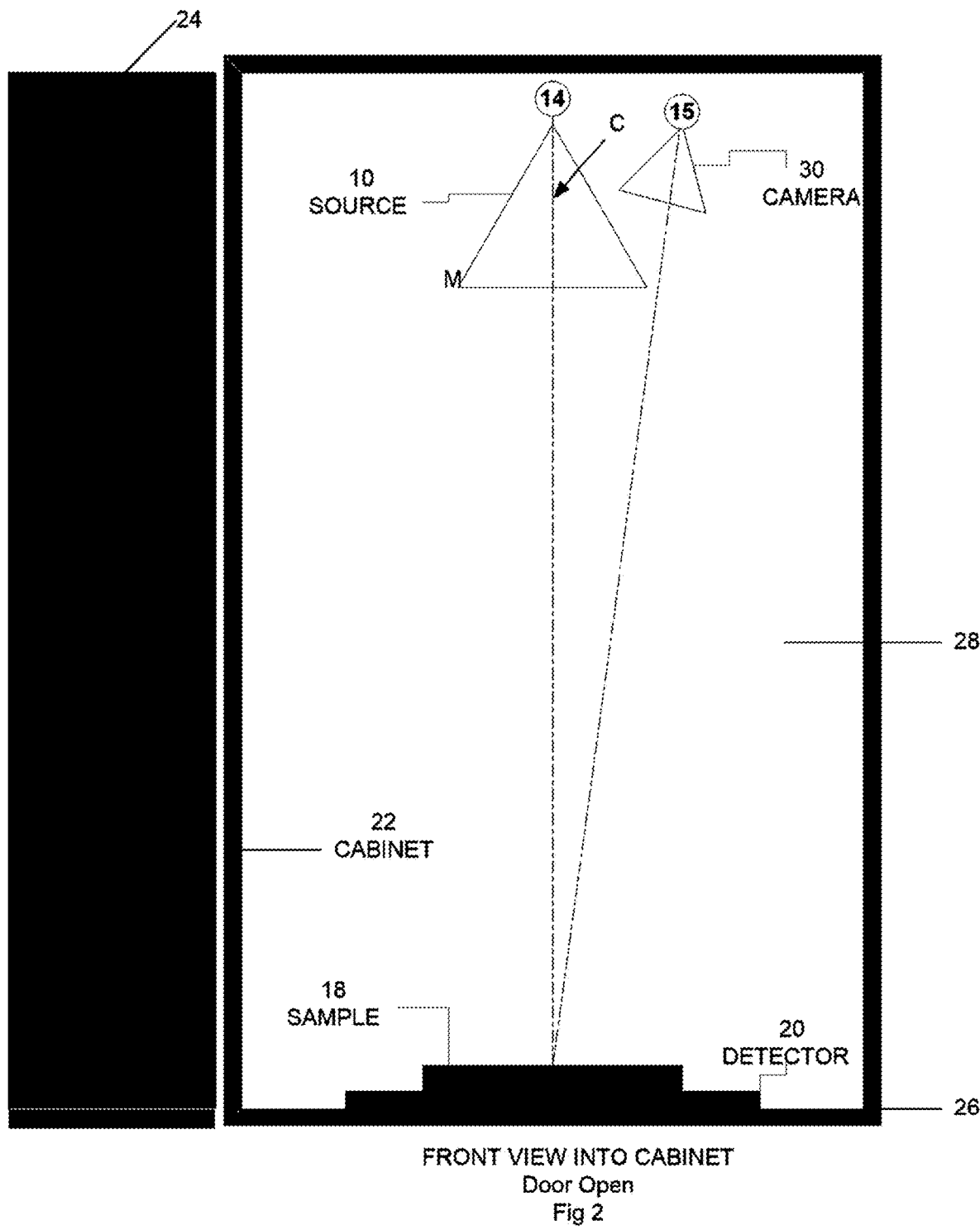
FIG. 2—Schematically illustrates an exemplary orientation of the x-ray source, specimen, and digital detector as viewed when the door of the cabinet is open, in one embodiment of a system incorporating aspects of the present disclosure.

FIG. 2 schematically illustrates one embodiment of the orientation of the X-ray source 10 as seen when the door 24 is opened and the X-ray source 10 is locate at approximately 0°, reference point 14 in this example, within the X-ray cabinet 22. In this embodiment, the motion of the X-ray source 10 can generally occur from the back to the front of the X-ray cabinet 22 with the detector 20 oriented, or otherwise disposed, at the base 26 of the X-ray cabinet 22, within the X-ray cabinet chamber 28. In one embodiment, the detector 20 is suitably coupled to the base 26 of the X-ray cabinet 22. The X-ray spread in this example can be from about 0 kVp to about 50 kVp with the system preferably utilizing an AEC (Automatic Exposure Control) to ascertain the optimal setting to image the object or sample 18 being examined.

In one embodiment, the detector 20, X-ray source 10, and the swing arm 60 (FIG. 5) servo mechanism as well as the optical camera and probe systems of the present disclosure are controlled via a combination of one or more of software and hardware, such as non-transitory machine-readable instructions stored in a memory that are executable by one or more processors. On example of such a configuration can include controller cards of a computer 470 (FIG. 4), such as a MS Windows based computer. In one embodiment, non-transitory machine readable instructions being executed by one or more processors of the computer 470 is utilized to compile data received from the detector 20 and present resulting images to a suitable display or monitor 472 (FIG. 4) at each imaging position, such as positions 12, 14 and 16 shown in FIG. 1, the detector 20 generates the respective digital values for the pixels in a two-dimensional array. The size of detector 20 may range, for example, from about 5.08 centimeters by 5.08 centimeters to about 40.64 centimeters by 40.64 centimeters, preferably about 12.7 centimeters by 15.24 centimeters. In one example, detector 20 has a rectangular array of approximately 1536×1944 pixels with a pixel size of 74.8 micrometers. The image dataset attained at each respective position may be processed either at the full spatial resolution of detector 20 or at a lower spatial resolution by overlapping or binning a specified number of pixels in a single combined pixel value.

For example, if we bin at a 2×2 ratio, then there would be an effective spatial resolution of approximately 149.6 micrometers. This binning may be achieved within the original programming of the detector 20 or within the computer 470 providing the tomosynthetic compilation and image.

Figure 3:
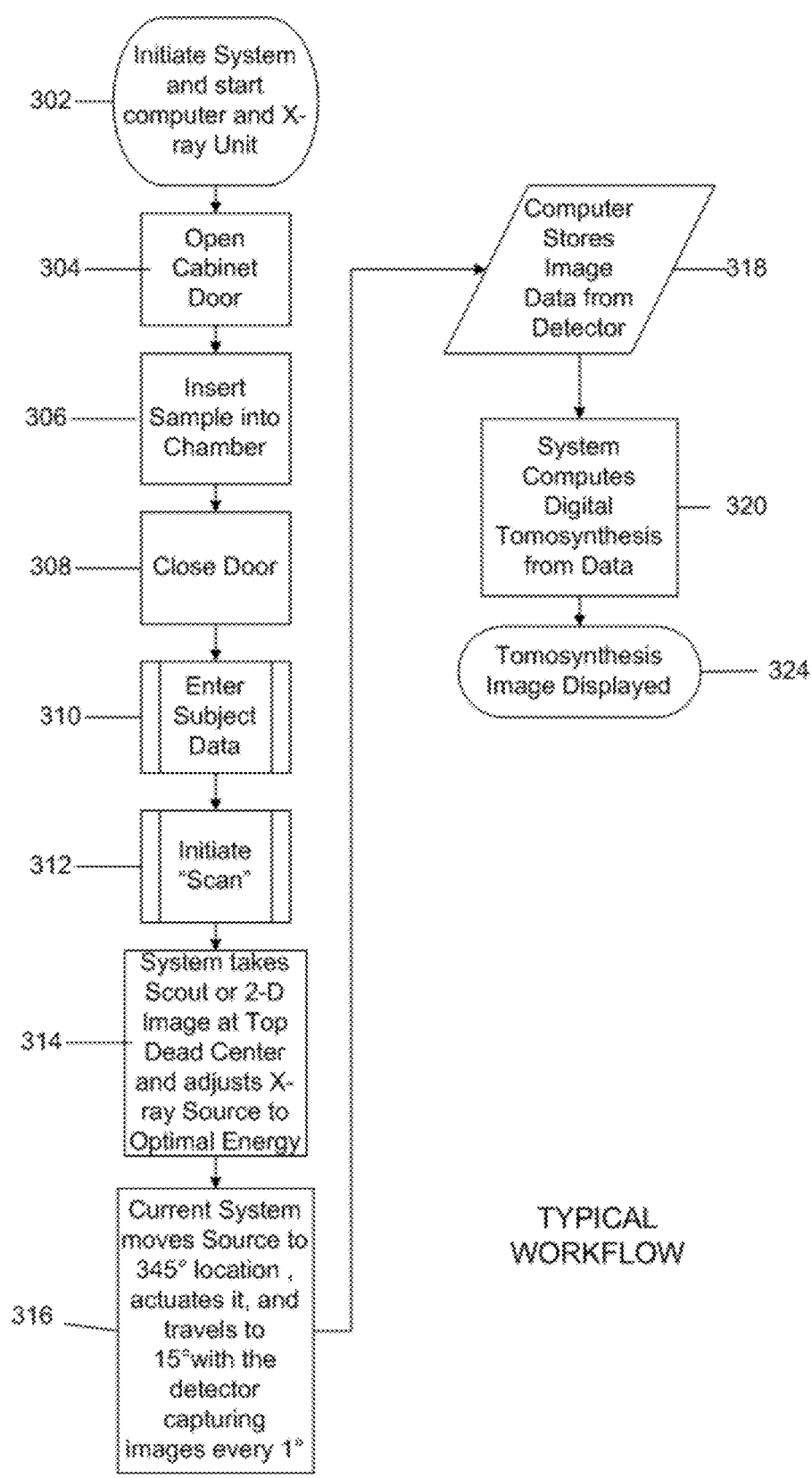
FIG. 3—Displays an exemplary workflow/flowchart of an aspect of the disclosed embodiments.

FIG. 3 illustrates one embodiment of an exemplary workflow from initiating 302 the system 100 through imaging, reconstruction and display 324 of data images collected of the sample 18.

As will be generally understood, the system 100 is initiated 302, the X-ray cabinet door 24 opened 304, and the sample 18 placed into 306 the X-ray cabinet chamber 28. As shown in FIG. 2, for example, the sample 18 is positioned on the detector 20 in a suitable manner. The door 24 is closed 308.

The data and information regarding the sample 18, including any other suitable information or settings relevant to the imaging process and procedure, is entered 310 into the computer 470. The scan is initiated 312. The system 100 will take 314 scout or 2-D images at Top Dead Center, which for purposes of this example is position 14 of FIGS. 1 and 2. The X-ray source 10 can then be moved to other positions using, for example, the swing arm 60 (FIG. 5) with servo mechanism (the latter connected to and motion controlled by, for example, computer 470) to which the x-ray source is mounted, such as positions 12 and 16, and the detector 20 can be used to capture 316 images at various increments along the travel path of the X-ray source 10, such as about every 1 degree.

The captured images are stored 318 and digital tomosynthesis is performed 320. The tomosynthesis image is then displayed 324.

Other embodiments of a system 100 incorporating aspects of the present disclosure are illustrated in FIGS. 1 and 2 where system 100 is totally enclosed or housed in an x-ray cabinet 22 and the x-ray source 10 is stationary relative to the stationary sample, 18 and can be used to obtain a 2-D image. In these embodiments, x-ray source 10 can be positioned at position 14 and the reference "C" refers to the point source of the x-ray beam and the reference "M" refers to the spread or fan of the x-ray beam. While the detector 20 may move or rotate, in accordance with one aspect of the present disclosure, the detector 20 can remain stationary relative to the sample 18 and x-ray source 10 to maintain an equidistant center point. The sample 18 also referred to as the "object" or "imaging object" may be disposed on or rest on the specimen platform 19 (which is a protective cover) or other surface of the detector 20. As with the previous embodiments described herein, the aspects of the present disclosure differ from the prior art in that in prior art systems either the detector and x-ray source 10 and/or the isocenter is above the sample and not at the detector surface. In operation, source 10 is energized to emit an x-ray beam at position 14, located at approximately 0°, and thereby obtain a 2-D image of sample 18. In operation, source 10 is energized to emit an x-ray beam, generally throughout its travel along one or more of the paths or positions described above. The x-ray beam travels through the sample 18 to the detector 16 and a 2-D image is stored. The x-ray source 10 may range from about 0 kVp to about 90 kVp, preferably a 50 kVp 1000 μa x-ray source.

Figure 4:
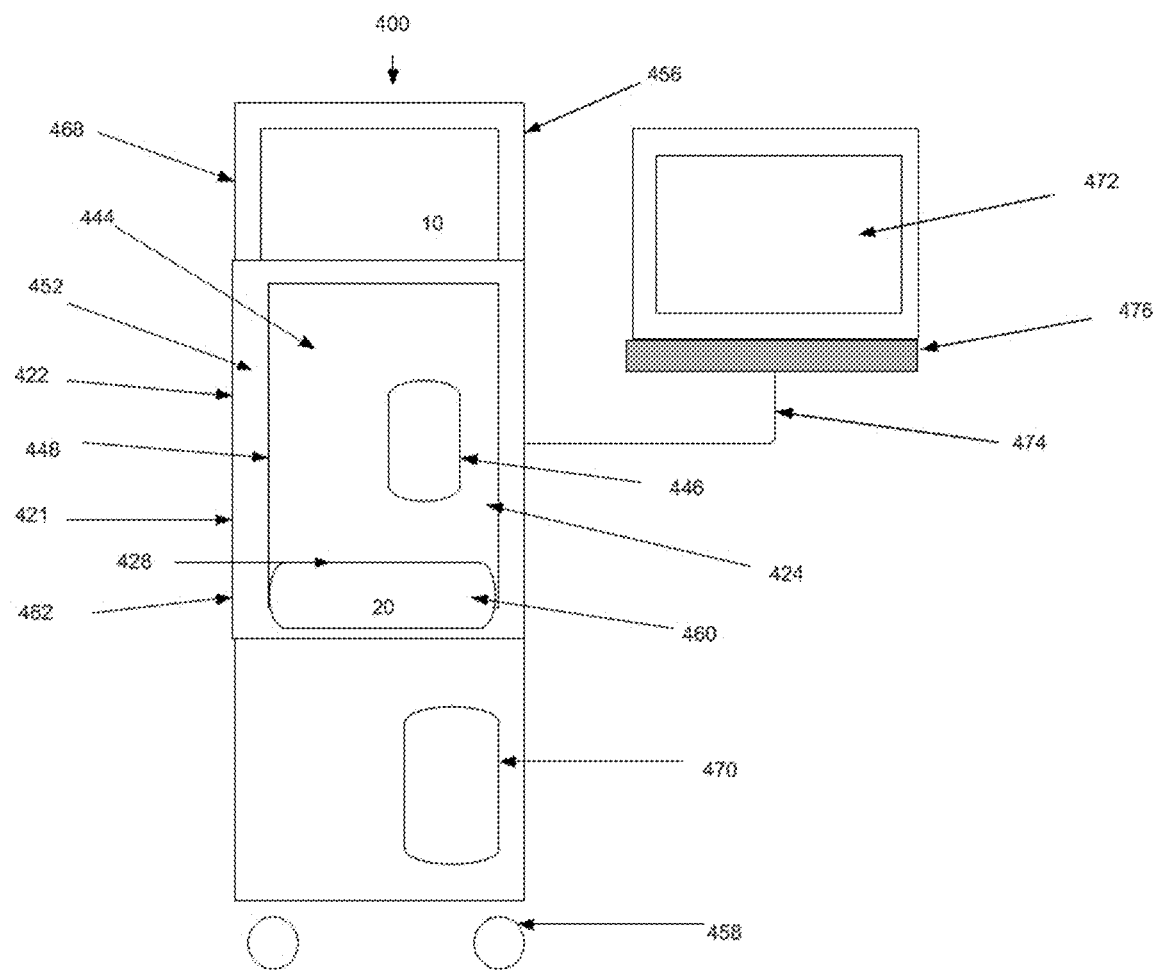
FIG. 4—Displays an example of an x-ray Cabinet System incorporating aspects of the present disclosure.

FIG. 4 shows one embodiment of an X-ray Cabinet System 400 incorporating aspects of the present disclosure. In this embodiment, the X-ray Cabinet System 400 is mounted on wheels 458 to allow easy portability. In alternate embodiments, the X-ray Cabinet System 400 can be mounted on any suitable base or transport mechanism. The cabinet 422 in this example, similar to the exemplary X-ray cabinet 22 of FIG. 1, is constructed of a suitable material such as steel. In one embodiment, the cabinet 422 comprises painted steel defining a walled enclosure with an opening or cabinet chamber 428. Within the cabinet chamber 428, behind door 424, resides an interior space forming a sample chamber 444, which in this example is constructed of stainless steel. Access to the sample chamber 444 is via an opening 446. In one embodiment, the opening 446 of the sample chamber 444 has a suitable door or cover, such as a moveable cover 448. In one embodiment, the moveable cover 448 comprises a door which has a window of leaded glass.

Between the outer wall 421 of cabinet 422 and the sample chamber 444 are sheets of lead 452 that serve as shielding to reduce radiation leakage emitted from the X-ray source 10. In the example of FIG. 4, the X-ray source 10 is located in the upper part 456 of the cabinet 422, in the source enclosure 468. The detector 20 is housed in the detector enclosure 460 at an approximate midpoint 462 of the cabinet 422.

Figure 5:
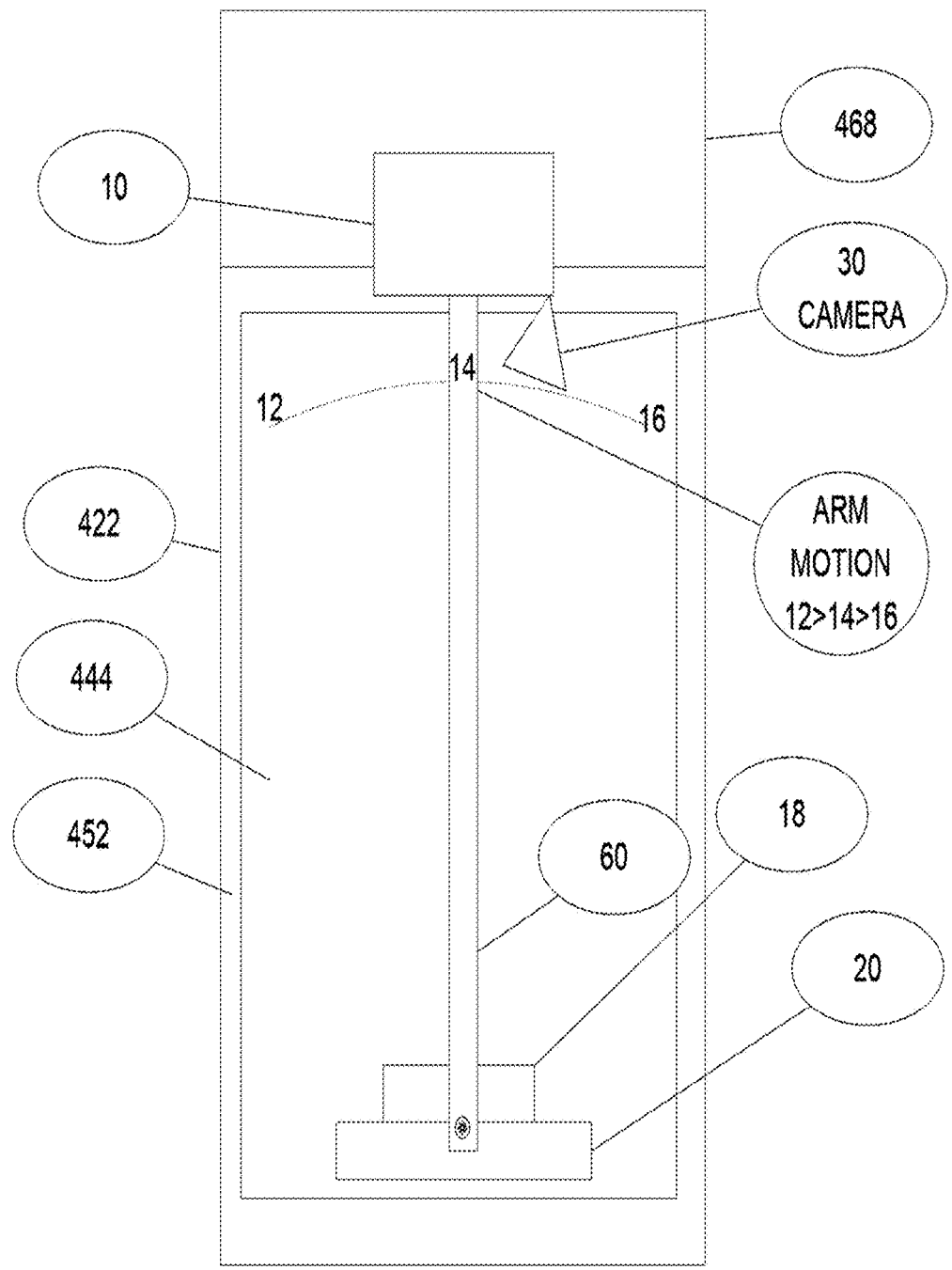
FIG. 5—Displays the sample chamber of the embodiment of FIG. 4 with the swing arm and a detector.
Figure 6:
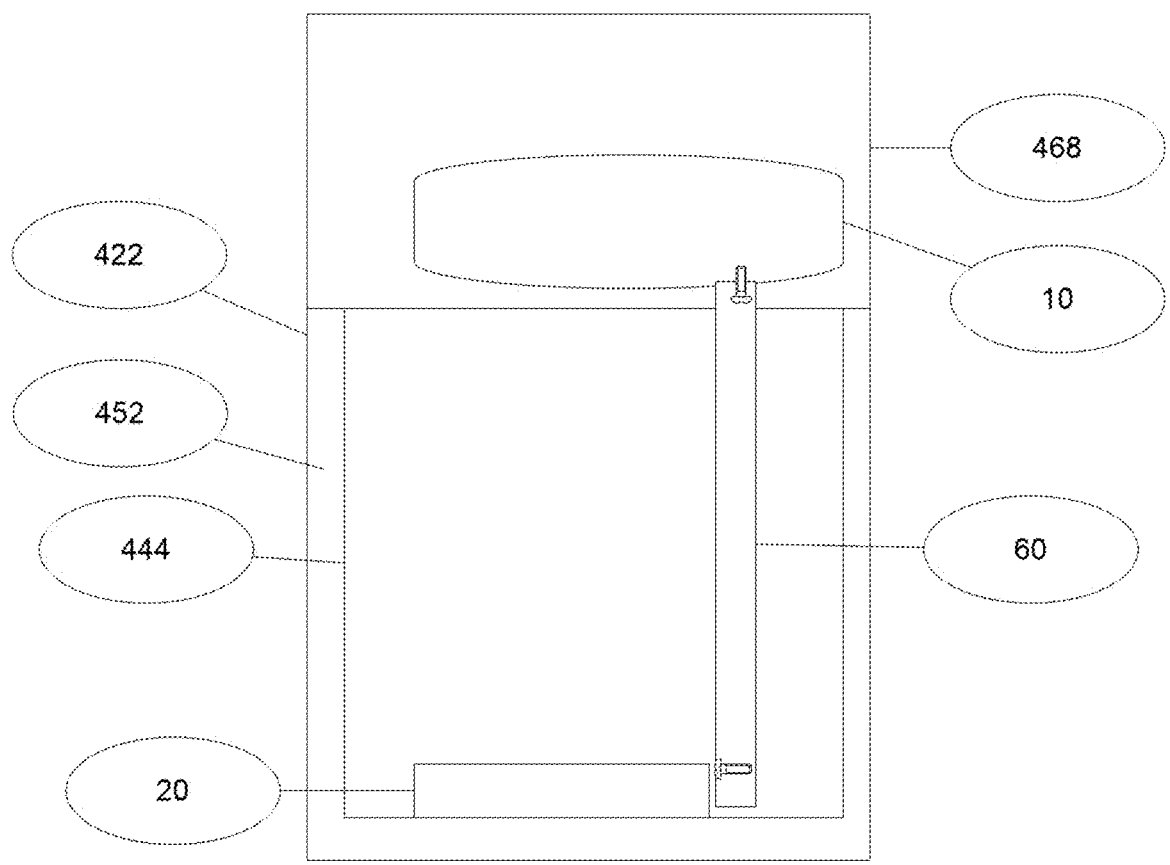
FIG. 6—Displays the lateral view of the x-ray source of the embodiment of FIG. 4 mounted to the top of the swing arm.

In one embodiment, a controller or computer 470 controls the collection of data from the detector 20, controls the swing arm 60 shown in FIGS. 5 & 6, and X-ray source 10. A monitor 472 displays the compiled data and can, for example, be mounted on an articulating arm 474 that is attached to the cabinet 422. The computer 470 receives commands and other input information entered by the operator via a user interface 476, such as a keyboard and mouse for example. In one embodiment, the computer 470 can comprise a touch screen or near touch screen device. Although the aspects of the disclosed embodiments will generally be described with respect to a computer 470, it will be understood that the computer 470 can comprise any suitable controller or computing device. Such computing devices can include, but are not limited to, laptop computers, minicomputers, tablets and pad devices.

The computer 470 can be configured to communicate with the components of the X-ray cabinet system 400 and X-ray cabinet system 1400 in FIG. 14 in any suitable manner, including hardwired and wireless communication. In one embodiment, the computer 470 can be configured to communicate over a network, such as a Local Area Network or the Internet.

FIG. 5 shows a front interior view and FIG. 6 shows a lateral interior view of the sample chamber of imaging unit cabinet of FIG. 4. In this embodiment, a sample 18 is placed or otherwise disposed onto the detector 20. Using the computer 470 shown in FIG. 4, the operator enters in the parameters for the scan via the user interface 476, which can be displayed on the monitor 472. As used herein, the term "display" or "monitor" means any type of device adapted to display information, including without limitation CRTs, LCDs, TFTs, plasma displays, LEDs, and fluorescent devices. The computer 470 then sends the appropriate commands to the X-ray source 10 and detector 20 to activate image collection while the swing arm 60 is moving as a result of the servo mechanism disclosed above along a path or arc from position 14 to 12 to 16 (which are shown in FIGS. 1 and 5) or vice versa as described, which in this embodiment are at 345°, 0°, and 15° respectively with 0° at top dead center. At the end of the travel of the swing arm 60 at either position 12 or 16, the computer 470 issues the command to the X-ray source 10 and the detector 20 to cease operating. The individual 2-dimensional (2-D) images which were collected, in this example at 1° increments, are then tabulated in the computer 470 to create the tomosynthetic images. In one embodiment, the operator may select which images of the images of the embodiments of the present disclosure they wish via the user interface 476 as they are being displayed on the monitor 472. In one embodiment, the devices and components of the X-ray cabinet system 400 are suitably communicatively coupled together, including one or more of hard wire connections or wireless connections using a suitable wireless connection and communication transmission protocol, as will generally be understood. The X-ray cabinet system 400 can also be configured to transfer images via USB, CD-ROM, or WIFI.

The dynamic imaging software of the disclosed embodiments reconstructs three-dimensional images (tomosynthesis) from two-dimensional projection images in real-time and on-demand. The software offers the ability to examine any slice depth, tilt the reconstruction plane for multiplanar views and gives higher resolution magnifications.

Figure 7A:
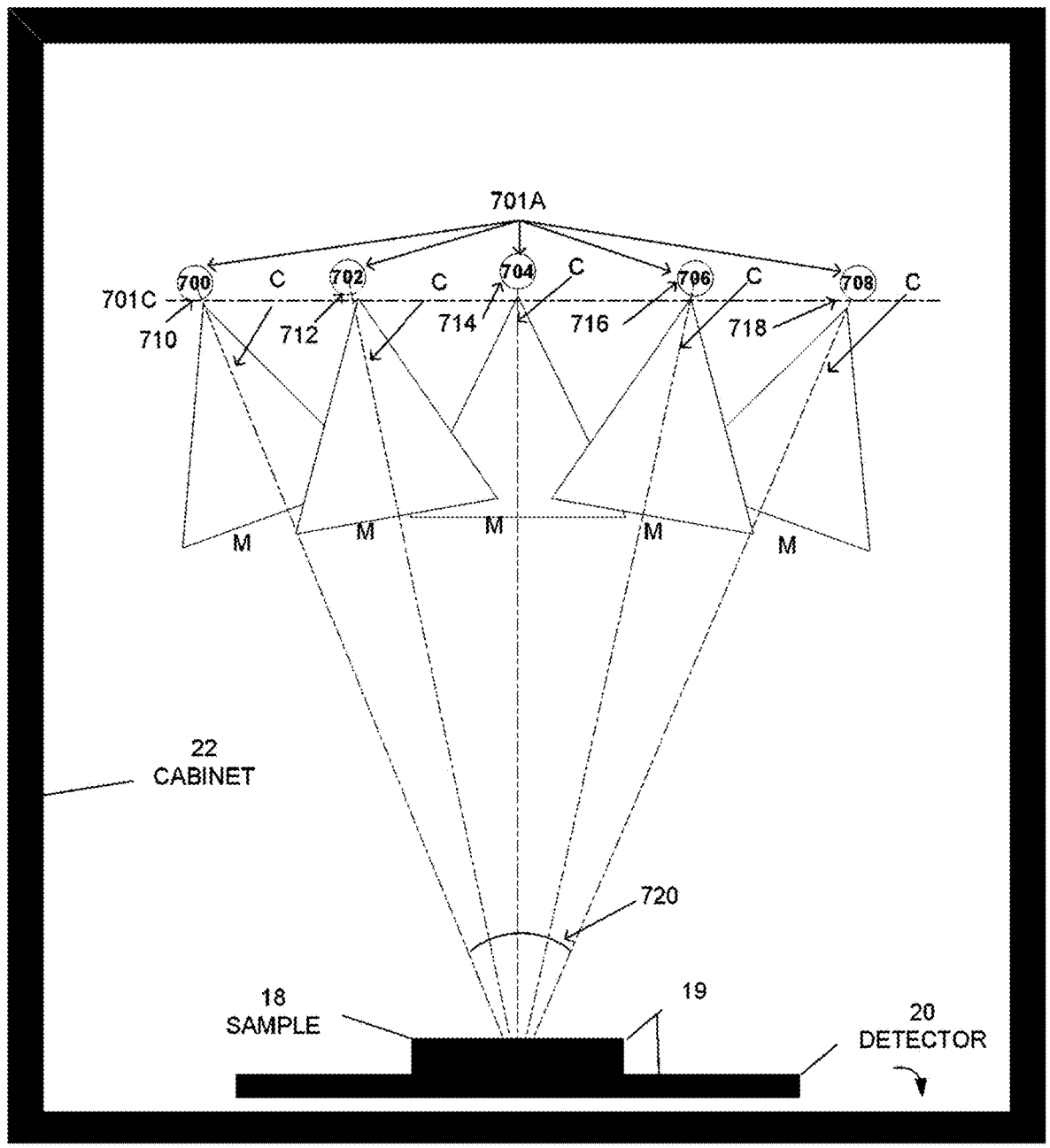
FIG. 7A—Schematically illustrates another embodiment of the present disclosure including a front view of a multitude of fixed X-ray sources, a specimen/sample, and a digital detector, where the X-ray source moves relative to the specimen for imaging the specimen at different angles, in one embodiment of a system incorporating aspects of the present disclosure.
Figure 7B:
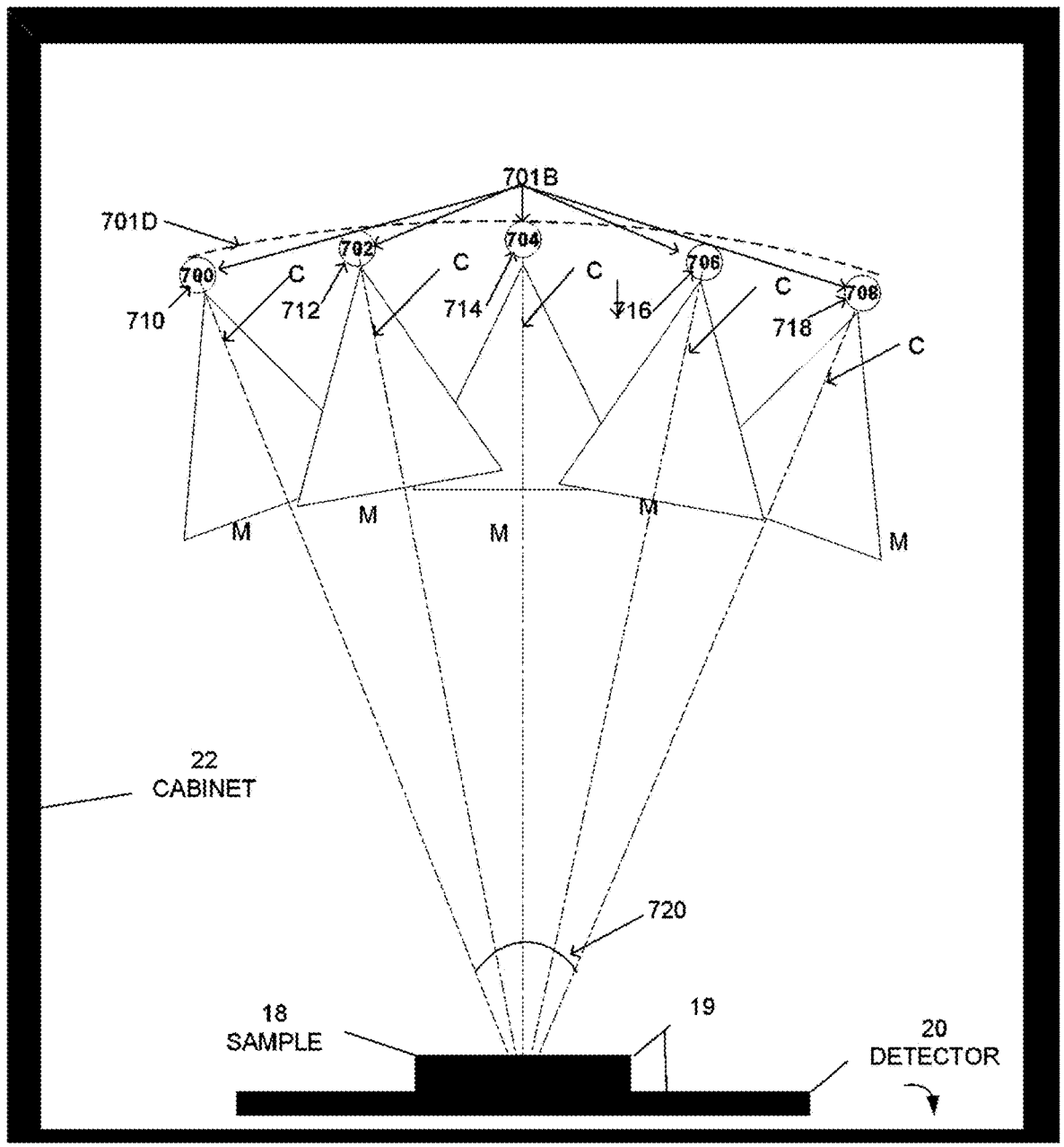
FIG. 7B—Schematically illustrates another embodiment of the present disclosure including a front view of a multitude of fixed X-ray sources, a specimen/sample, and a digital detector, where the X-ray source moves relative to the specimen for imaging the specimen at different angles, in one embodiment of a system incorporating aspects of the present disclosure.

Another embodiment of the present disclosure is illustrated in FIGS. 7A and 7B that operate and include the aspects and features illustrated in the embodiments of FIGS. 1-6 except the embodiments of FIGS. 7A and 7B include an array or plurality of fixed x-ray sources at fixed points, for example, x-ray sources 700, 702, 704, 706 and 708 in place of the travel of x-ray source 10 moving (FIG. 1) swing arm 60 (FIG. 5) servo mechanism. 710, 712, 714, 716 and 718 illustrate exemplary positions of x-ray sources 700, 702, 704, 706 and 708, respectively. An optical camera and probe system similar to those included in the present disclosure can be incorporated into the embodiments in FIGS. 7A and 7B as they are incorporated into other embodiments of the present disclosure.

The aspects of the embodiments illustrated in FIGS. 7A and 7B include at least one array or plurality of x-ray sources 701A positioned in a linear shaped arrangement along substantially linear axis 701C, as shown in FIG. 7A or at least one array or plurality of x-ray sources 701B positioned in an arc shaped arrangement along arc or curved axis 701D, as shown in FIG. 7B. The reference "C" at each of the x-ray sources 700, 702, 704, 706 and 708 in FIGS. 7A and 7B refers to the point source of the X-ray beam from each x-ray source. The reference "M" refers to the spread or fan of the X-ray beam from each x-ray source.

X-ray sources 700, 702, 704, 706 and 708 can be distributed at positions 710, 712, 714, 716 and 718, respectively, in FIGS. 7A and 7B with the end positions of the array, for example, between the point source "C" line of the beam of 700 at position 710 and the point source "C" line of the beam of 708 at position 718, are separated by an arc 720 of from about 20° to about 50°, preferable about 30°, more preferable about 20° with one x-ray source, for example, the point source "C" line of the beam of 704 at position 714 positioned at about 0°. The other x-ray sources 702 at position 712, and 706 at position 716 can be positioned such that each of those x-ray sources are positioned in between x-ray sources 700 and 708 along linear axis 701C, as shown in FIG. 7A or arc or curved axis 701D, as shown in FIG. 7B, preferably evenly spaced. The following are exemplary positions for the embodiments of FIGS. 7A and 7B can be used. Exemplary Configuration 1—about 350° (reference position 710), about 355° (reference position 712), about 0° (reference position 714), about 5° (reference position 716) and about 10° (reference position 718); Exemplary Configuration 2—about 340° (reference position 710), about 350° (reference position 712), about 0° (reference position 714), about 10° (reference position 716) and about 20° (reference position 718); Exemplary Configuration 3—about 335° (reference position 710), about 347.5° (reference position 712), about 0° (reference position 714), about 12.5° (reference position 716) and about 25° (reference position 718); between approximately 340° (reference position 12) to 0° (reference position 14) to 20° (reference position 16) and or between approximately 335° (reference position 12) to 0° (reference position 14) to 25° (reference position 16).

In another embodiment, X-ray sources 700, 702, 704, 706 and 708 can be positioned at 710, 712, 714, 716 and 718, respectively, in FIGS. 7A and 7B, such that the point source "C" line of the beam of each the x-ray sources at either end of the array, the point source "C" line of the beam of 700 at position 710 and the point source "C" line of the beam of 708 at position 718, are separated by an arc 720 of from about 20° to about 50° arc, preferable about 30°, more preferable about 20°, with one x-ray source the point source "C" line of the beam of 704 at position 714 is positioned at about 0°. The other x-ray sources 702 at position 712, and 706 at position 716 can be positioned such that the point source "C" of the beam of each of those x-ray sources are positioned within arc 720, preferable with the point source "C" line of the beams of x-ray sources 702 at position 712, 704 at position 714 and 706 at position 716 are evenly distributed between the point source "C" line of the beam x-ray sources 700 at position 710 and 708 at position 718. For example, x-ray source 700 can be positioned with a point source "C" line of the beam thereof at about 350°, x-ray source 702 can be positioned with a point source "C" line of the beam thereof at about 355°, x-ray source 704 can be positioned with a point source "C" line of the beam thereof at about 0°, x-ray source 706 can be positioned with a point source "C" line of the beam thereof at about 5° and x-ray source 708 can be positioned with a point source "C" line of the beam thereof at about 10°. For another example, x-ray source 700 can be positioned with a point source "C" line of the beam thereof at about 340°, x-ray source 702 can be positioned with a point source "C" line of the beam thereof at about 350°, x-ray source 704 can be positioned with a point source "C" line of the beam thereof at about 0°, x-ray source 706 can be positioned with a point source "C" line of the beam thereof at about 10° and x-ray source 708 can be positioned with a point source "C" line of the beam thereof at about 20°. For still another example, x-ray source 700 can be positioned with a point source "C" line of the beam thereof at about 335°, x-ray source 702 can be positioned with a point source "C" line of the beam thereof at about 347.5°, x-ray source 704 can be positioned with a point source "C" line of the beam thereof at about 0°, x-ray source 706 can be positioned with a point source "C" line of the beam thereof at about 12.5° and x-ray source 708 can be positioned with a point source "C" line of the beam thereof at about 25°.

The ranges recited herein are intended to be approximate and inclusive of start and endpoints.

The number of x-ray sources in the arrays or pluralities of x-ray sources 701A and 701B can range from a minimum total of at least about 3 to about 11 or more, about 5 to about 11 (preferably about 5, about 7, about 9, about 11) including preferably an odd number of x-ray sources, further including for each of these aforementioned ranges wherein one of the x-ray sources is positioned at about 0° or the point source "C" line of one of the x-ray beams is positioned at about 0°. An alternative embodiment can include arrays or pluralities of x-ray sources 701A and 701B distributed such that the point sources of adjacent x-ray sources in the array or plurality are separated by about 1° to about 5°, preferably about 1°. As with other embodiments of the present disclosure the x-ray detector 20 is stationary as is the sample 18 and the x-ray detector can include, for example, a flat panel x-ray detector including a flat panel digital x-ray detector. The x-ray cabinet 22, the detector 20, the sample 18 and the specimen platform 19 (which is a protective cover) or other surface of the detector 20 are the same as included in the embodiment of FIG. 1. As with other embodiments of the present disclosure, the isocenter of the image acquisition geometry is located below the sample, on the surface of the detector.

Each x-ray source of the array or plurality (e.g., x-ray sources 700, 702, 704, 706 and 708) can be activated to emit an x-ray beam one at a time so that the detector 20 receives only one image at a time. The sequence of activating the x-ray sources can be random, but preferably, from left to right (e.g., first 700, second 702, third 704, fourth 706 and fifth 708) or right to left (e.g., first 708, second 706, third 704, fourth 702 and fifth 700).

Operation of the embodiments of FIGS. 7A and 7B that is different from what is included in the present disclosure in FIG. 3 includes at 316 the detector 20 capturing images from x-rays emitted from each of the fixed x-ray sources ((e.g., x-ray sources 700, 702, 704, 706 and 708) that are included in the array or plurality of x-ray sources and storing the captured image along with the identification of the specific x-ray source ((e.g., x-ray sources 700, 702, 704, 706 and 708) from which it originated, using the latter information to identify the position of the x-ray source relative to the sample. The captured images and identification of the specific x-ray source ((e.g., x-ray sources 700, 702, 704, 706 and 708) from which each originated are stored 318 and digital tomosynthesis is performed 320. The tomosynthesis image is then displayed 324.

One advantage of having a fixed array of x-ray sources (compared to, for example, having one x-ray source that is moved by, e.g., a motion control mechanism) is the elimination of moving parts needed to move the single x-ray source, the elimination of vibration caused by x-ray source movement during use which could cause blurring or artifacts, the faster acquisition of x-ray images as energizing each of the plurality of x-ray sources need only rely on computer controlled (e.g., computer 470) and don't need to wait until the single x-ray source is moved into position, and a more precise angle resolution because each of the x-ray source in the plurality or array are fixed in position rather than having to rely on a moving x-ray source where its position can be less precise during operation.

The real-time image reconstruction of the present disclosure enables immediate review, higher throughput, and more efficient interventional procedures reducing patient call backs and data storage needs. Multiplanar reconstruction enables reconstruction to any depth, magnification and plane, giving the viewer the greater ability to view and interrogate image data, thereby reducing the likelihood of missing small structures. Built-in filters allow higher in plane resolution and image quality during magnification for greater diagnostic confidence. Software is optimized for performance using GPU Technology.

The reconstruction software used in conjunction with the aspects of the present disclosure provides the users greater flexibility and improved visibility of the image data. It reconstructs images at any depth specified by the user rather than at fixed slice increments. With fixed slice increments, an object located between two reconstructed slices, such as a calcification, is blurred and can be potentially missed. The aspects of the present disclosure provide for positioning the reconstruction plane so that any object is exactly in focus. This includes objects that are oriented at an angle to the detector 20. The aspects of the present disclosure provide for the reconstruction plane to be angled with respect to the detector plane.

Figure 8:
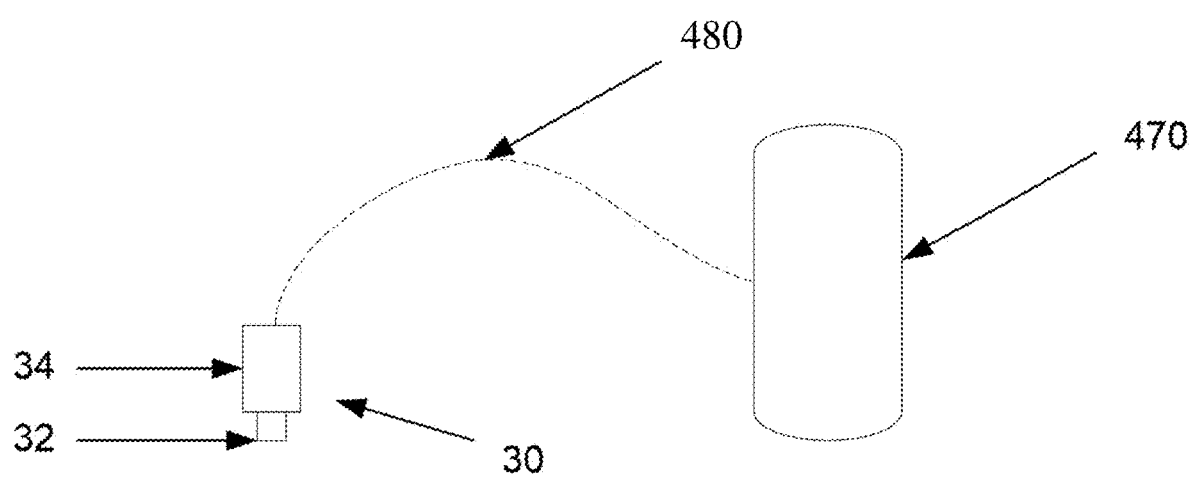
FIG. 8—Displays an interconnection diagram of an HD camera embodiment that may be utilized in aspects of the disclosed embodiments of the present disclosure.
Figure 9:
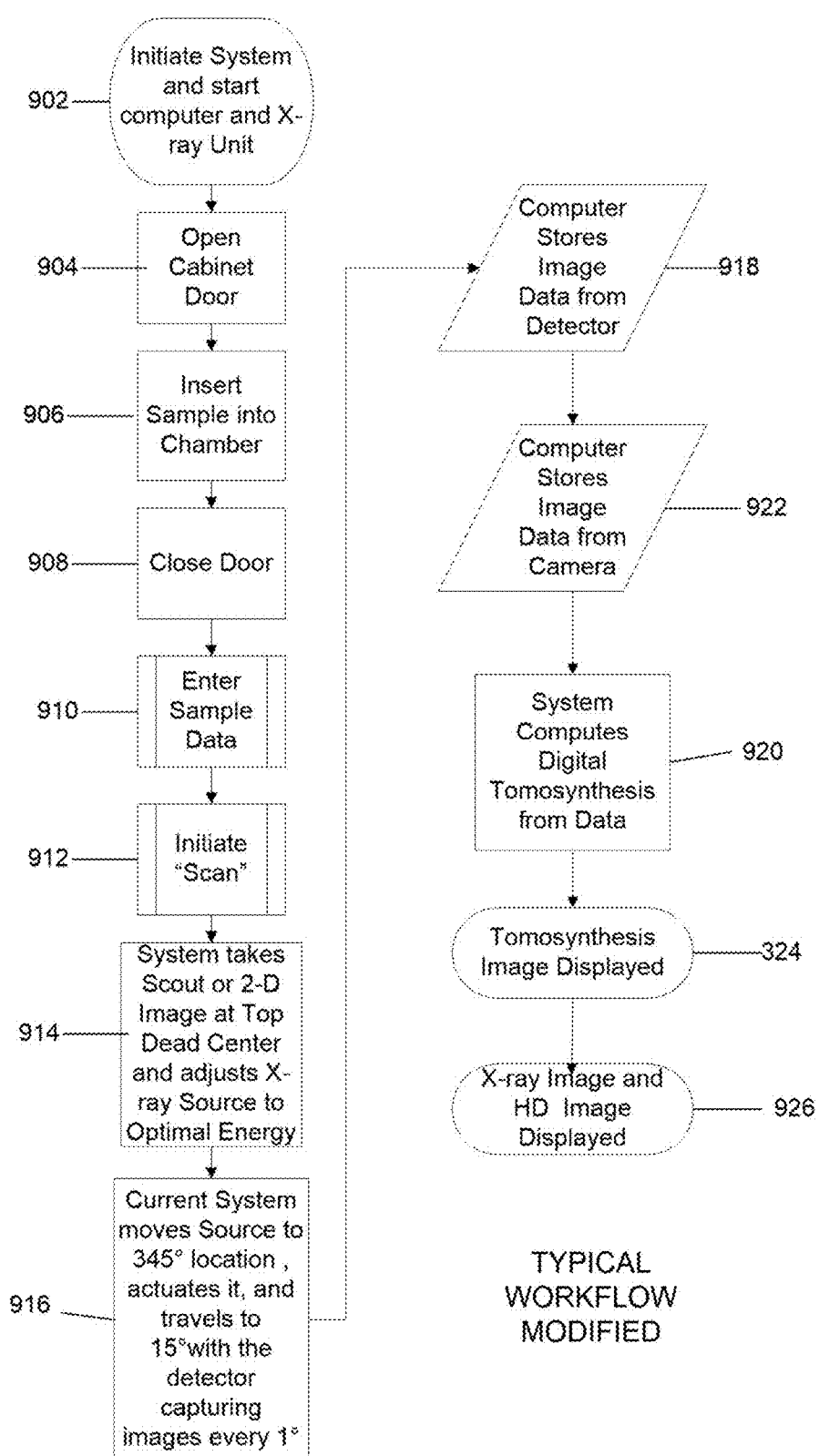
FIG. 9—Displays an exemplary modified workflow/flowchart of an aspect of the disclosed embodiments.

FIGS. 8 and 9 depict various features of embodiments of the present disclosure, which embodiments are generally directed to a system that can utilize an optical camera, preferably a real-time camera, to capture a visual image of a specimen/sample concurrently or at substantially the same time as the acquisition of an x-ray image. Referring to FIG. 8, there is shown the interconnection of an embodiment of a camera 30 incorporated into a Cabinet X-Ray Unit which connects to and can be controlled by the computer 470 via cable 480 including, for example a USB cable. Other wireless formats for communication between camera 30 and computer 470 can also be used in embodiment of the present disclosure. Camera 30 may include an optical lens assembly 32 through which an optical image passes and is focused upon an electronic light-sensitive sensory array included in the camera body 34. The optical image can then be sent using an electronic signal from the sensory array to the computer 470 via cable 480 or other wireless formats. The optical image as well as a 2-D x-ray image or tomosynthesis image can also be stored in the computer 470 for future examination and viewing, including storage in memory (e.g., RAM) or a disc recording medium (e.g., CD, DVD, etc.)

Camera 30 is included in FIGS. 1, 2 and 5 as well showing embodiments in camera 30, for example, located at position 15 in the cabinet x-ray unit such that it is capable of capturing a visual image of sample 18 in cabinet 22 and x-ray cabinet chamber 28 in FIGS. 1 and 2 and in cabinet 422 and sample chamber 444 in FIG. 5, preferably such that the optical image captured by camera and the x-ray image (2-D x-ray image or tomosynthetic x-ray image) show the sample or specimen at substantially, preferably exactly, the same orientation for the optical and x-ray images. In one embodiment, a medical professional or other authorized operator places a specimen/sample into the chamber, closes and secures the door, and presses, for example, the "acquire" command on the system using, for example, a keyboard or touch screen monitor that can be used to enter system commands or other information. In one embodiment, pressing this command can simultaneously or in substantially close proximity in time, the computer commands the optical camera, the probe system and x-ray source in conjunction with the x-ray detector to capture images from the three components, the latter being an x-ray image or series of images from which tomosynthetic images can be assemble. In another embodiment, as a result of pressing this command, the x-ray source in conjunction with the x-ray detector captures an x-ray image or series of images from which tomosynthetic images can be assemble. The resulting x-ray image or tomosynthetic image can them be displayed at the same time as or separately from a real-time optical image is captured through the camera and examined in conjunction with data (e.g., audio or visual readout) from the probe system of the present disclosure.

FIG. 9 illustrates one embodiment of a modified basic workflow of the cabinet x-ray unit with the addition of the storage of the image data 922 and the combination x-ray image and HD image displayed 926.

As will be generally understood, the system 100 is initiated 902, the X-ray cabinet door 24 opened 904, and the sample 18 placed into 906 the X-ray cabinet chamber 28. As shown in FIG. 2, for example, the sample 18 is positioned on the detector 20 in a suitable manner. The door 24 is closed 908.

The data and information regarding the sample 18, including any other suitable information or settings relevant to the imaging process and procedure, is entered 910 into the computer 470. The scan is initiated 912. The system 100 will take 914 scout or 2-D images at Top Dead Center, which for purposes of this example is position 14 of FIGS. 1 and 2. The X-ray source 10 can then be moved to other positions, such as positions 12 and 16, and the detector 20 can be used to capture 916 images at various increments along the travel path of the X-ray source 10, such as about every 1 degree. An optical image, for example, an HD image, is captured by the camera and stored in the computer 922. The captured images are stored 918 and digital tomosynthesis is performed 920. The tomosynthesis image is then displayed 924. The combination x-ray image and HD image are then displayed 926, the x-ray image can be either the 2-D image from 914 or the tomosynthesis image from 920. Another embodiment of the workflow embodiment illustrated in FIG. 9 can include obtaining a 2-D x-ray image as in 914 without the detector 20 being used to capture 916 images at various increments along the travel path and related steps 920 and 924 related to tomosynthesis.

Another embodiment includes superimposition of an optical image such as that stored in step 922 of FIG. 9 or in real-time and at least one of the x-ray images stored or in real-time including the 2-D image from 914 or the tomosynthesis image from 920 also from FIG. 9 to form a superimposed image. An image blender can be used to perform the superimposition of the images and form one or more superimposed images upon which superimposition can be performed. Superimposition and the combination of two images allows for an adjustment of the degree of opacity and, as a result, the degree of transparency of at least one of the two images, preferably the top image (e.g., the optical image including, for example, an HD optical image) that is displayed on top of and covering the lower image (e.g., the x-ray image including a 2-D image or a tomosynthesis image) so that to the viewer, the top image is positioned between the lower image and the viewer's eye and the lower image can be viewed through the top image. With superimposition and the adjustment thereof, the greater the opacity of the top image, the lesser the detail shown of the lower image and lesser the opacity of the top image, the greater the detail shown of the lower image. Each of the images as part of the superimposition image adjustment shown may be also adjusted utilizing window levelling or brightness and contrast to accentuate or visualize the fiduciary item or structure.

The image blender controls the superimposition process and can receive images in real-time images, stored images or a combination of both. The superimposed image can be viewed on a suitable display or monitor 472 (FIG. 4). Single or multiple superimposed images at various levels of opacity can also be viewed on the display or stored in in the computer hard drive on the system 470 or a separate memory device, such as for example, a separate hard drive, flash drive, CD-ROM, DVD, etc. for future analysis.

Another embodiment can include the image blender aligning the optical image and the x-ray image for superimposition. The alignment of the images can include, for example, taking the lower image (e.g., an x-ray image) as background layer and placing the top image (e.g., an optical including an optical HD image) on top of the lower image. The image blender can also move and zoom the top image to align it with lower image according to a calibration file included in the image blender (The location and zoom factor of top image layer can be calibrated in prior to the alignment). The user can then adjust to change the opacity of top layer using, for example, a slide bar including, for example, a horizontal slider.

Figure 10B:
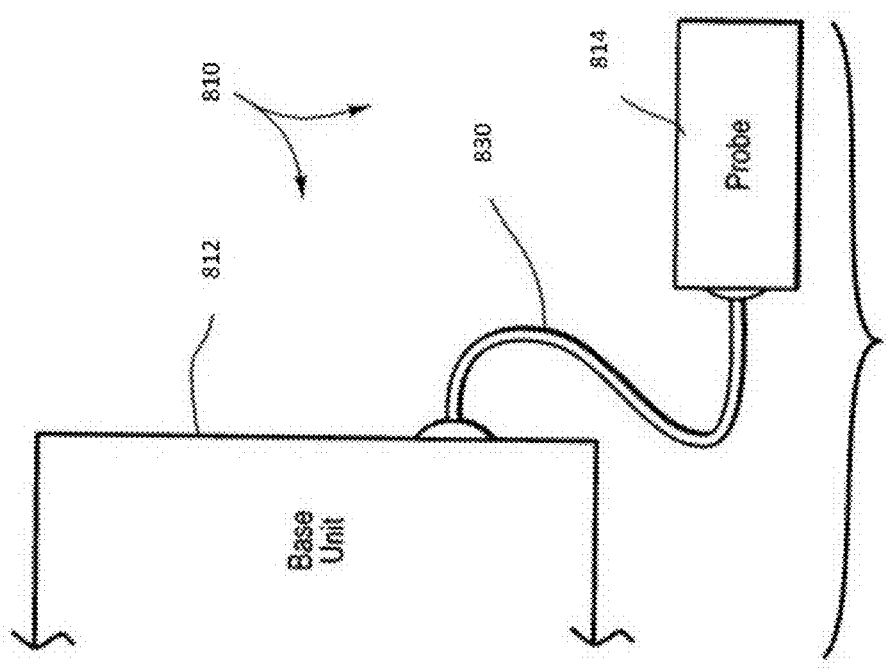
FIG. 10B is a simplified view of a portion of FIG. 1A in accordance with an alternative example embodiment.
Figure 10A:
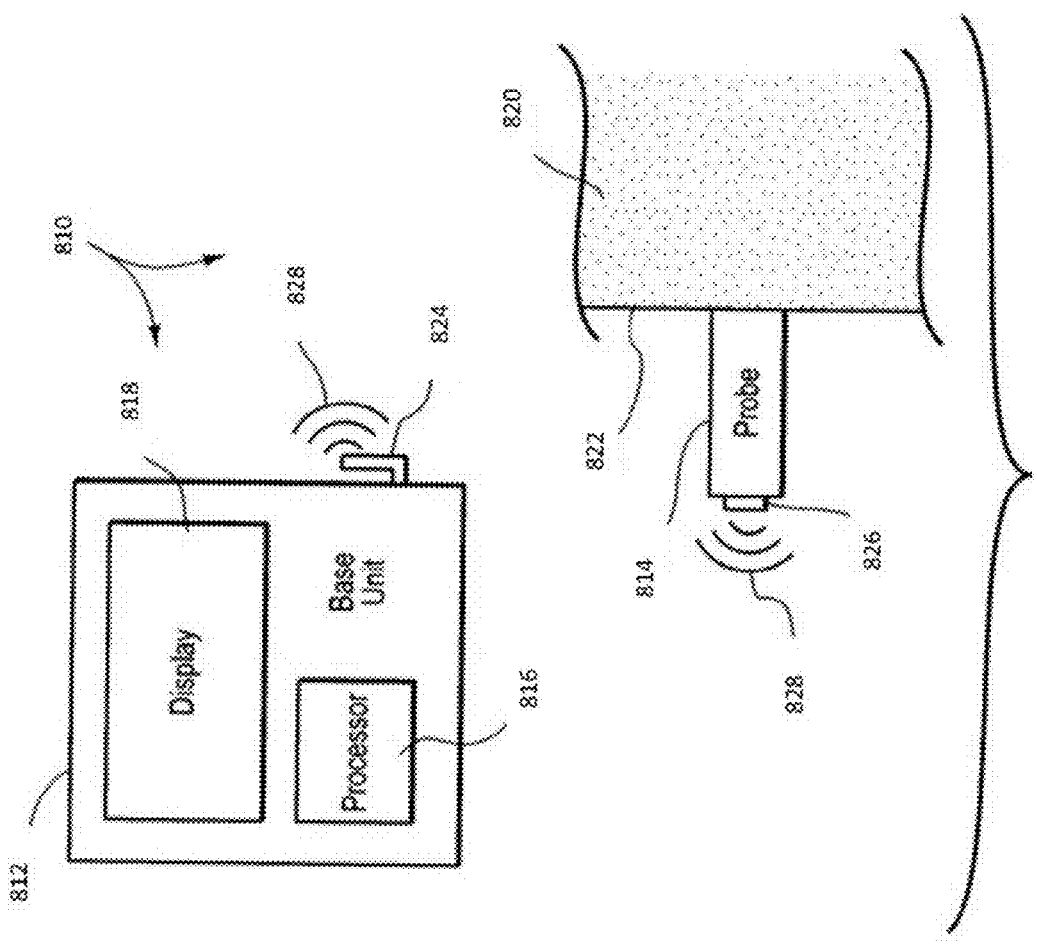
FIG. 10A is a simplified diagram of a Gamma or other probe system configured in accordance with one example embodiment of the present disclosure.
Figure 10C:
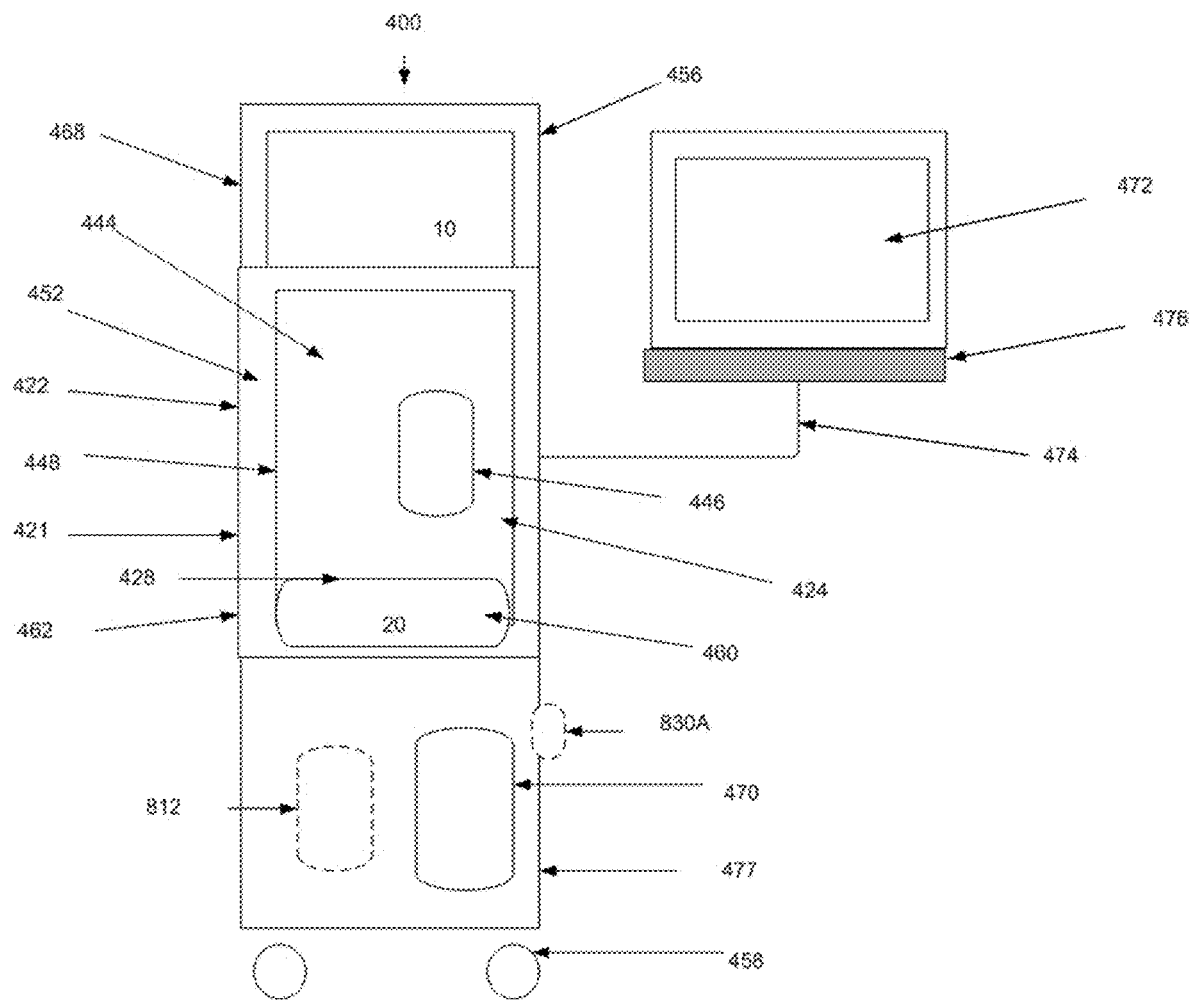
FIG. 10C illustrates another embodiment example of an x-ray Cabinet System incorporating aspects of the present disclosure.

FIGS. 10A, 10B and 10C depict various aspects of embodiments of the present disclosure that include various features of embodiments of the present disclosure, which embodiments are generally directed to a system for performing Gamma Probe (e.g., radioactive detection of the radioactive seeds in the body of a patient or other subject) incorporated into a cabinet x-ray unit. FIG. 10A, displays how the probe 814 after wirelessly connecting with the base unit 812 and FIG. 10B displays how the probe 813 connects with the base unit 812 via a tether 830. FIG. 10C shows the cabinet and it's components and sub structures. Advantageously, the system to be described requires relatively low power levels in order to function, thereby enabling the system to take advantage of wireless technologies to untether the Gamma Probe from the base unit of the system. This, in turn, provides more flexibility for a clinician or other user of the system and simplifies the detection procedure.

Aspects of one embodiment are shown in FIG. 10A, that shows a gamma probe system 810, preferably a low power gamma probe system for the reason included herein. As shown, the gamma probe system ("system") 810 generally includes a base unit 812 and a gamma probe 814. The gamma probe 814 can also include a local power source (e.g., a battery or rechargeable power supple unit) for the embodiment of FIG. 10A or for the embedment of FIG. 10B, can received power from the base unit 812 via cable 830. The base unit 812 may include a processor 816 for performing processing functions on emission data retrieved by the gamma probe 814 during, for example, a sentinel node or radioactive localization procedure. FIG. 10A also shows the gamma probe 814 placed adjacent a surface 822 of a body 820 of a patient or other subject. Though understood to be used in applications such as that shown here in FIG. 10A, it is also appreciated that embodiments of the present disclosure may be modified for use with gamma probes having other shapes and configurations, including probes configured for penetration into an orifice of the patient, for instance. The gamma probe 814 receives an external radiated signal (e.g., radioactive emissions) and sends an electronic signal corresponding to the external radiated signal to the base unit 812. The base unit 812 may further include a display or monitor 818. The electronic signals processed by the processor 816 of the base unit 812 and received from the probe 814 (e.g., signals, including, for example, the amount of radioactivity corresponding to the external signals received and detected by probe 814) can be presented as a visual analogue or digital numerical readout on the display 818 of, for example, the amount of radioactivity received and detected by probe 814. The gamma probe system 810 may also include a sound output or audio feature (e.g., a sound generator) that provides audible sounds (e.g., a beep) in a series such that with the higher amounts of external radiated signal (e.g., radioactivity) received and detected by probe 814, the closer together in time the sounds are spaced and the lower amounts of external radiated signal (e.g., radioactivity) received and detected by probe 814, the farther away in time the sounds are spaced. As a result, the medical professional operation the embodiments of the present disclosure can receive an audio indication when the amount of external radiated signal (e.g., radioactivity) received and detected by probe is increasing or decreasing as the probe is moved. Indeed, it is appreciated that the gamma probe system 810 and its individual components can include additional features and components, though not disclosed herein, while still preserving the principles of the present disclosure. Note also that the base unit 812 can be one of any number devices, including, for example, a dedicated gamma probe device or a desktop or laptop computer, such as that, for example, computer 470 in FIG. 4.

The base unit 812 can also be connected to computer 470 and integrated into x-ray cabinet system 400. In the presently depicted embodiment, the gamma probe system 810 implements wireless technology, wherein the base unit 812 and the probe 814 are in two-way, wireless communication with one another. To that end, the base unit 812 includes a base antenna 824 that wirelessly communicates with a gamma probe antenna 826 included with the gamma probe 814. Wireless signals 828, representing electromagnetic communication such as, for example, RF, WIFI, Wireless USB, IEEE 802.x, WIMAX, or Bluetooth signals between the base unit 812 and the gamma probe 814, can be used. In this way, external radiated signals detected by the probe 814 and their corresponding electronic signals can be wirelessly transmitted by the probe antenna 826 to the base unit 812 via the base antenna 824 for processing by the processor 816. Coupling of the probe and base unit (including the components thereof) can be accomplished using one or more of hard wire (e.g., cable) connections or wireless connections using a suitable wireless connection and communication transmission protocol or non-wireless, or even hybrid wireless/cabled communication link, as will generally be understood. Note that one or more of a variety of wireless data transfer protocols, including Wireless USB, IEEE 802.x, BLUE TOOTH, WIMAX, etc., may be employed for such data transfer as described herein. FIG. 10B represents another possible embodiment, wherein the base unit 812 of the gamma probe system 810 that is communicatively coupled with the gamma probe 814 not wirelessly, but via a cable 830. As such, it is appreciated that the gamma probe system as described herein may be employed with a wireless, non-wireless, or even hybrid wireless/cabled communication link between the base unit and the probe.

Aspects of another embodiment is shown in FIG. 10C that includes a cabinet system 400 with base unit 812 which may be positioned in an equipment enclosure 477 of the cabinet system 400 along with computer 470. Base unit 812 can include processor 816 and display 818 is display driver as shown in FIG. 10A. In this embodiment, base unit 812 can include base antenna 824 as shown in FIG. 10A or can be hard wire connected to the connection point 830A. Connection point 830A can, in turn, be a cable connector for the cable 830 for gamma probe 814 in FIG. 10B or an antenna similar to base antenna 824 for gamma probe 814 in FIG. 10A. Base unit 812 in FIG. 10C, can be connected through display 818 when its display driver is directly to monitor 472 or indirectly to monitor 472 when the display driver is connected to computer 470.

Figure 11:
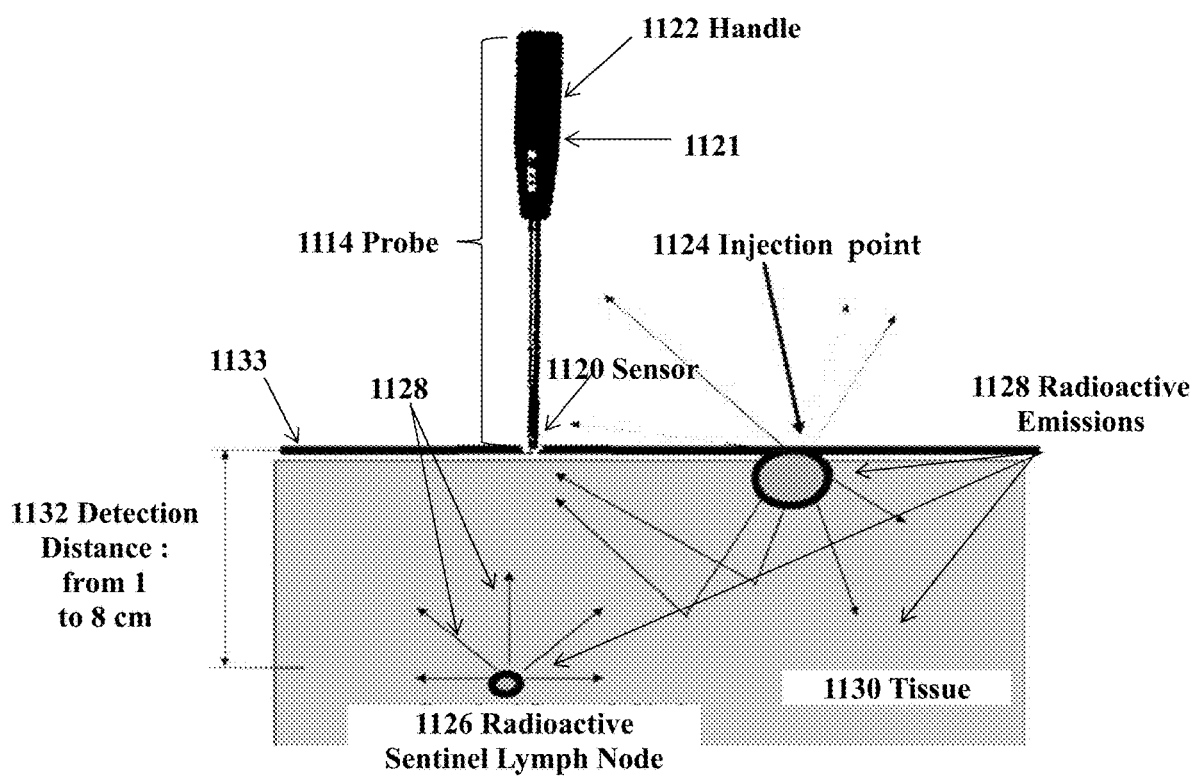
FIG. 11 is a display of typical utilization of a Gamma or other probe in tissue by the probe in FIG. 10A.

Reference is now made to FIG. 11, which depicts various details and embodiments regarding the gamma probe 1114 of the system 810 shown in FIGS. 10A and 10B. As depicted, the gamma probe 1114 according to the present embodiment is a wireless probe, however, this is for the purpose of showing exemplary use and embodiments using a wired probe can also be used similarly and includes a probe housing 1121 that includes a handle 1122 that acts as a covering for various internal components of the probe. A sensor head 1120 with a handle 1122 is included in the gamma probe 1114 and houses the array of sensors that act as transducers to enable detection of the radioactive emissions 1128 of an object within the tissue 1130 of the patient to be detected within the distance 1132 of 1-8 cm from the skin or tissue surface 1133 during such seed localization procedures. Tissue 1130 can be present in the body of a patient before it is excised or as a separate object after being excised from the body of the patient. Other than radioactive emissions, emissions or other signals from other tags or seeds can be used and implanted, such as, for example, metallic/magnetic seed material, or an RFD transmitter. Such seeds or tags can be implanted in tissue to identify tumors or tissue areas containing tumors or other cancerous lesions so that during surgery, the surgeon can identify the tissue to be excised.

For example, the technical features of the gamma probe can include the following: detector CsI scintillating crystal doped with thallium+PM tube or +photodiode; reusable wireless probe; integrated collimator; best in class shielding more than 99% for 99mTc; energy detected between 40 and 511 keV; 1 cm sensitivity >13.000 cps/MBq, 1 cm resolution; 3 cm sensitivity >1.900 cps/MBq, 3 cm resolution; length/Diameter 11.4" (290 mm)/0.5" (12 mm); Weight 0.44 lbs (200 g); Multi-isotope detection 99mTc, I125; original sound rate highly visible digital display 6 digits; Control unit connections Ethernet, RJ45, USB, Bluetooth.

In one embodiment, sentinel node localization can be performed using for example, Technetium 99, a radioactive isotope, is injected at point 1124 where point 1124 is near or adjacent a tumor. The radioactive isotope can pass through the tumor and into lymph nodes to which the tumor is anatomically connected. The gamma probe 1114 is used to scan to detect the emissions 1128 of the Technetium 99 or other radionuclide as it courses through the patient's body from the tumor and identify lymph nodes (e.g., radioactive sentinel lymph node 1126) that need to be removed along with the tumor because cancerous cells from the tumor may have passed therethrough. The Technetium 99 or other radionuclide that has been injected and the emissions radiating from the injection point 1124 can be absorbed by the sentinel lymph node and the gamma probe can be used to identify its location by detecting the emissions from the sentinel lymph node 1126.

Thus, it is appreciated that the probe 1114 as shown in FIG. 11 can be desirably included within the sterile field of a patient undergoing a procedure in preparation for a lumpectomy for instance. Note that the particular design of the probe 1114 as shown in FIG. 11, together with the specified location for the various components thereof both internal and external can be varied such that the size, look, and configuration of the probe may be modified from what is explicitly shown as displayed in FIG. 11.

The external radiated signals and corresponding electronic signals as received by the base unit and processed by the processor 816 can be used to form an a sound output as well as an numerical signal display indication (analogue or digital on a display) of the external radiated signals received from the scanned object 1126 and detecting the emissions 1128. All of the above Gamma or other probe components, in this embodiment, can be incorporated into a cabinet x-ray unit FIG. 10C with system 400 incorporating base unit 812 and the embodiments of FIG. 10A or 10B and visually displaying the emission signal as previously mentioned with regard to FIGS. 10A-10C and features thereof including monitor 472, user interface 476, arm 474 and base unit 812. The present disclosure may be embodied in other specific forms without departing from its spirit or essential characteristics. The described embodiments are to be considered in all respects only as illustrative, not restrictive. All changes that come within the meaning and range of equivalency of the claims are to be embraced within their scope.

Other embodiments of the present disclosure include methods utilizing of the equipment, system and apparatus embodiments of the present disclosure. An embodiment of the present disclosure may also include a method including a medical professional using an embodiment of the present disclosure to obtain and/or store a two-dimensional (2-D) x-ray image or a synthetic x-ray image assembled from more than one x-ray image (e.g., a tomosynthetic image) of a specimen, visually examining the two-dimensional (2-D) x-ray image or the synthetic x-ray image assembled from more than one x-ray image (e.g., a tomosynthetic image) of the specimen on a monitor or display to determine the location of anatomical features (e.g., lumps, tumors or other anatomical abnormalities or markers (e.g., implanted markers), using that information to scan the specimen for external radiated signals (e.g., radioactivity, RFID, magnetic metal object, etc. included in the present disclosure) using a gamma or other probe of the present disclosure and recording or making note of the magnitude of the signal detected by the gamma or other probe and its location at different locations thereof on the specimen either by direct observation or using an optical image of a specimen (e.g., in real time) using an optical camera.

Another embodiment of the present disclosure includes include methods utilizing the equipment, system and apparatus embodiments of the present disclosure. An embodiment of the present disclosure may also include a method including a medical professional using a gamma or other probe of the present disclosure to scan the cancerous area of a patient and recording or making note of the magnitude of the signal detected by the gamma or other probe and its location at different locations thereof. Next excising a tissue specimen where the gamma or other probe signals were detected. Then, use an embodiment of the present disclosure to obtain and/or store a two-dimensional (2-D) x-ray image or a synthetic x-ray image assembled from more than one x-ray image (e.g., a tomosynthetic image) of the excised specimen, visually examining the two-dimensional (2-D) x-ray image or the synthetic x-ray image assembled from more than one x-ray image (e.g., a tomosynthetic image) of the excised specimen on a monitor or display to determine the location of anatomical features (e.g., lumps, tumors or other anatomical abnormalities or markers (e.g., implanted markers), using that information to scan the specimen for external radiated signals (e.g., radioactivity, RFID, magnetic metal object, etc. included in the present disclosure) using a gamma or other probe of the present disclosure and recording or making note of the magnitude of the signal detected by the gamma or other probe and its location at different locations thereof on the specimen either by direct observation or using an optical image of a specimen (e.g., in real time) using an optical camera.

Another embodiment of the present disclosure includes include methods utilizing the equipment, system and apparatus embodiments of the present disclosure. Another embodiment of the present disclosure may also include a method including a medical profession visually examining an optical image of an excised specimen (e.g., in real time) on a monitor or display using an optical camera, using a gamma or other probe of the present disclosure to scan the specimen for external radiated signals (e.g., radioactivity, RFID, magnetic metal object, etc. included in the present disclosure) while continuing to visually examine the optical image and recording or making note of the magnitude of the external radiated signal detected by the gamma or other probe as provided by embodiments of the present disclosure and its magnitude at different locations thereof on the specimen while observing the optical image of the specimen (e.g., in real time) using the optical camera.

Another embodiment of the present disclosure includes include methods utilizing the equipment, system and apparatus embodiments of the present disclosure. Another embodiment of the present disclosure may also include a method including a medical profession using an embodiment of the present disclosure to obtain and store a two-dimensional (2-D) x-ray image or a synthetic x-ray image assembled from more than one x-ray image (e.g., a tomosynthetic image) of an excised specimen (the x-ray obtained images), the medical professional visually examining an optical image of the specimen (e.g., in real time) on a monitor or display using an optical camera also including on the monitor or display the stored two-dimensional (2-D) x-ray image or a synthetic x-ray image assembled from more than one x-ray image (e.g., a tomosynthetic image) of the specimen (the x-ray obtained images) in, for example, side-by-side, picture in picture or with one of the optical or x-ray obtained images superimposed on the other of the two images to determine the location of anatomical features (e.g., lumps, tumors or other anatomical abnormalities or markers (e.g., implanted markers) to use that information to scan the specimen for signals (e.g., radioactivity, etc. included in the present disclosure) using a gamma or other probe of the present disclosure, using a gamma or other probe of the present disclosure to scan the specimen for signals (e.g., radioactivity, etc. included in the present disclosure) while continuing to visually examining the images on the display or monitor and recording or making note of the magnitude of the signal detected by the gamma or other probe and its location at different locations thereof on the specimen. This embodiment may also include changing the opacity of one of the optical or x-ray obtained images before or during the step of using the gamma or other probe.

An embodiment of the present disclosure may also include a method including superimposing on the display or monitor an optical image of the specimen (e.g., in real time) on top of the stored two-dimensional (2-D) x-ray image or a synthetic x-ray image assembled from more than one x-ray image (e.g., a tomosynthetic image) of the specimen (the x-ray obtained images) where the optical and stored two-dimensional (2-D) x-ray image or a synthetic x-ray image show the specimen at the same orientation and such that the opacity of one of the optical image is changed to that features of the stored two-dimensional (2-D) x-ray image or a synthetic x-ray image are at least partially visible through the optical image and the gamma or other probe is manipulated by medical professional with such manipulation and the gamma or other probe itself are visible in the optical image as well as optionally, the hands, for example, of the medical professional in contact with the gamma or other probe. As a result, some features of the specimen visible in the stored two-dimensional (2-D) x-ray image or a synthetic x-ray image can be used by the medical professional to guide that person's movement of the gamma or other probe to obtain signals (e.g., radioactivity, etc. included in the present disclosure) therefrom and locate specific areas of the specimen (e.g., tumor or other abnormalities labeled or tagged in the specimen).

All publications, including but not limited to, issued patents, patent applications, and journal articles, cited in this application are each herein incorporated by reference in their entirety.

Thus, while there have been shown, described and pointed out, fundamental novel features of the present disclosure as applied to the exemplary embodiments thereof, it will be understood that various omissions and substitutions and changes in the form and details of devices and methods illustrated, and in their operation, may be made by those skilled in the art without departing from the spirit or scope of the present disclosure. Moreover, it is expressly intended that all combinations of those elements and/or method steps, which perform substantially the same function in substantially the same way to achieve the same results, are within the scope of the present disclosure. Moreover, it should be recognized that structures and/or elements and/or method steps shown and/or described in connection with any disclosed form or embodiment of the present disclosure may be incorporated in any other disclosed or described or suggested form or embodiment as a general matter of design choice. It is the intention, therefore, to be limited only as indicated by the scope of the claims appended hereto.

This written description uses examples as part of the disclosure, including the best mode, and also to enable any person skilled in the art to practice the disclosed implementations, including making and using any devices or systems and performing any incorporated methods. The patentable scope is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

While there have been shown, described and pointed out, fundamental features of the present disclosure as applied to the exemplary embodiments thereof, it will be understood that various omissions and substitutions and changes in the form and details of compositions, devices and methods illustrated, and in their operation, may be made by those skilled in the art without departing from the spirit or scope of the present disclosure. Moreover, it is expressly intended that all combinations of those elements and/or method steps, which perform substantially the same function in substantially the same way to achieve the same results, are within the scope of the present disclosure. Moreover, it should be recognized that structures and/or elements and/or method steps shown and/or described in connection with any disclosed form or embodiment of the present disclosure may be incorporated in any other disclosed or described or suggested form or embodiment as a general matter of design choice. It is the intention, therefore, to be limited only as indicated by the scope of the claims appended hereto.

The invention claimed is:

1. A cabinet x-ray and gamma probe system for obtaining x-ray images and gamma probe measurements of a specimen, the system comprising:
   a cabinet defining an interior chamber;
   a first display;
   an x-ray system including:
      an x-ray source;
      an x-ray detector;
      a specimen platform; and
   a controller configured to:
      selectively energize the x-ray source to emit x-rays through the specimen to the x-ray detector;
      control the x-ray detector to collect a projection x-ray image of the specimen when the x-ray source is energized; and
      selectively display the x-ray image on the display; and
   a gamma probe system including:
      a gamma probe configured to receive external radiated signals from external sources and transmit electronic signals corresponding to the external radiated signals received to the gamma probe base unit; and
      a gamma probe base unit in communication with the gamma probe and including a processor, the processor configured to receive the electronic signals received from the gamma probe and present the electronic signals as at least one of a visual numerical readout on the first display, a visual numerical readout on a second display and generate a sound output.

2. The cabinet x-ray and gamma probe system of claim 1, wherein the cabinet comprises a walled enclosure surrounding the interior chamber, a door configured to cover the interior chamber and a sampling chamber within the interior chamber for containing the specimen.

3. The cabinet x-ray and gamma probe system of claim 1, wherein the specimen platform is configured for excised tissue, organ or bone specimens.

4. The cabinet x-ray and gamma probe system of claim 1, wherein the specimen platform is configured for any organic or inorganic specimen that fits inside an x-ray cabinet.

5. The cabinet x-ray and gamma probe system of claim 1, further comprising:
   the specimen platform having a protective cover of and in physical contact with the x-ray detector;
   a motion control mechanism configured for moving the x-ray source to or along a plurality of positions within the interior chamber relative to the specimen disposed on the specimen platform; and
   a controller further configured to:
      selectively energize the x-ray source to emit x-rays through the specimen to the x-ray detector at selected positions of the x-ray source relative to the specimen such that the isocenter of the emitted x-rays at the selected positions is located at a surface of the x-ray detector;
      control the x-ray detector to collect projection x-ray images of the specimen when the x-ray source is energized at the selected positions, wherein one of the projection x-ray images is a two-dimensional x-ray image taken at standard imaging angle of approximately 0°;
      create a tomosynthetic x-ray image reconstructed from a collection of projection x-ray images;
      process the collection of the projection x-ray images in the controller into one or more reconstructed tomosynthetic x-ray images representing a volume of the specimen and relating to one or more image planes that are selectively the same or different from that of the two-dimensional x-ray image; and
      selectively display the two-dimensional x-ray image and the one or more reconstructed tomosynthetic x-ray images on the display.

6. The cabinet x-ray and gamma probe system of claim 1, wherein the gamma probe and gamma probe base unit are in two-way communication with one another.

7. The cabinet x-ray and gamma probe system of claim 1, wherein the gamma probe and gamma probe base unit are in communication via at least one of a cable or a wireless system.

8. The cabinet x-ray and gamma probe system of claim 1, wherein the gamma probe base unit also includes a display driver that is configured to receive the gamma probe data signals from the processor and send the electronic signals to the controller, the controller configured to selectively display the electronic signals as a visual numerical readout on the display.

9. The cabinet x-ray and gamma probe system of claim 1, wherein the x-ray image and the visual numerical readout are concurrently displayed on the first display.

10. A cabinet x-ray, optical camera and gamma probe system for obtaining x-ray images, projection x-ray images, reconstructed tomosynthetic x-ray images, optical images and gamma probe measurements of a specimen, the system comprising:
a cabinet defining an interior chamber and an equipment enclosure;
a display;
an x-ray system including:
an x-ray source positioned in the interior chamber;
an x-ray detector positioned in the interior chamber;
a specimen platform positioned in the interior chamber configured to have the specimen positioned thereon and which is a protective cover of and in physical contact with the x-ray detector; and
a motion control mechanism positioned in the interior chamber and configured for moving the x-ray source to or along a plurality of positions within the interior chamber relative to the specimen disposed on the specimen platform;
a gamma probe system including:
a gamma probe configured to receive external radiated signals from external sources and transmit electronic signals corresponding to the external radiated signals received to the gamma probe base unit; and
a gamma probe base unit in communication with the gamma probe and including a processor, the processor configured to receive the electronic signals received from the gamma probe and send the electronic signals to a controller; and
an optical camera configured to capture an optical image of the interior chamber;
the controller positioned in the equipment enclosure and configured to:
selectively energize the x-ray source to emit x-rays through the specimen to the x-ray detector at selected positions of the x-ray source relative to the specimen such that the isocenter of the emitted x-rays at the selected positions is located at a surface of the x-ray detector;
control the x-ray detector to collect a projection x-ray images of the specimen when the x-ray source is energized at the selected positions, wherein one of the projection x-ray images is a two-dimensional x-ray image taken at standard imaging angle of approximately 0°;
create a tomosynthetic x-ray image reconstructed from a collection of projection x-ray images;
process the collection of the projection x-ray images in the controller into one or more reconstructed tomosynthetic x-ray images representing a volume of the specimen and relating to one or more image planes that are selectively the same or different from that of the two-dimensional x-ray image;
store the projection x-ray images and the one or more reconstructed tomosynthetic x-ray images;
control the optical camera to capture and collect an optical image of the specimen and the gamma probe in the interior chamber;
selectively display a superimposed image comprising a first image including the optical image in real time superimposed on top of a second image of the two-dimensional x-ray image or one of the reconstructed tomosynthetic x-ray images such that when the gamma probe is present in the interior chamber, the gamma probe and its movement relative to the specimen in the first superimposed image are displayed on the display;
selectively change the opacity of the first image of the first superimposed image to form a second superimposed image; and
selectively display the second superimposed image such that when the gamma probe is present in the interior chamber, the gamma probe and its movement relative to the specimen in the second superimposed image are displayed on the display.

11. The cabinet x-ray and gamma probe system of claim 10, wherein the cabinet comprises a walled enclosure surrounding the interior chamber, a door configured to cover the interior chamber and a sampling chamber within the interior chamber for containing the specimen.

12. The cabinet x-ray and gamma probe system of claim 10, wherein the specimen platform is configured for excised tissue, organ or bone specimens.

13. The cabinet x-ray and gamma probe system of claim 10, wherein the specimen platform is configured for any organic or inorganic specimen that fits inside an x-ray cabinet.

14. The cabinet x-ray and gamma probe system of claim 10, wherein the gamma probe and gamma probe base unit are in two-way communication with one another.

15. The cabinet x-ray and gamma probe system of claim 10, wherein the gamma probe and gamma probe base unit are in communication via at least one of a cable or a wireless system.

16. The cabinet x-ray and gamma probe system of claim 10, wherein the orientation of the specimen in the first image and the second image are substantially the same.

17. A method for obtaining an x-ray image and gamma probe measurements of a specimen in a cabinet x-ray and gamma probe system, processing and displaying the x-ray image and gamma probe system measurements of the specimen, wherein the cabinet x-ray and gamma probe system comprises:
a cabinet defining an interior chamber;
a first display;
an x-ray system including:
an x-ray source;
an x-ray detector; and
a specimen platform;
a controller configured to:
selectively energize the x-ray source to emit x-rays through the specimen to the x-ray detector;
control the x-ray detector to collect a projection x-ray image of the specimen when the x-ray source is energized; and
selectively display the x-ray image on the display; and
a gamma probe system including:

a gamma probe configured to receive external radiated signals from the specimen and transmit electronic signals corresponding to the external radiated signals received to the gamma probe base unit; and a gamma probe base unit in communication with the gamma probe and including a processor, the processor configured to receive the electronic signals received from the gamma probe and present the electronic signals as at least one of a visual numerical readout on the first display, a visual numerical readout on a second display and generate a sound output, wherein the method comprises:

controlling the x-ray detector to collect an x-ray image of the specimen when the x-ray source is energized;

controlling the gamma probe to receive the external radiated signals from the specimen and transmit the electronic signals corresponding to the external radiated signals received to the gamma probe base unit;

selectively displaying the x-ray image on the display; and selectively presenting the electronic signals received by the gamma probe base unit as at least one of a visual numerical readout on the first display, a visual numerical readout on a second display and generate a sound output.

18. The method of claim 17, comprising concurrently displaying the x-ray image and presenting the electronic signals received by the gamma probe system.

19. The method of claim 17, wherein the x-ray system further includes the specimen platform having a protective cover of and in physical contact with the x-ray detector;

a motion control mechanism configured for moving the x-ray source to or along a plurality of positions within the interior chamber relative to the specimen disposed on the specimen platform; and a controller further configured to:

selectively energize the x-ray source to emit x-rays through the specimen to the x-ray detector at selected positions of the x-ray source relative to the specimen such that the isocenter of the emitted x-rays at the selected positions is located at a surface of the x-ray detector;

control the x-ray detector to collect projection x-ray images of the specimen when the x-ray source is energized at the selected positions, wherein one of the projection x-ray images is a two-dimensional x-ray image taken at standard imaging angle of approximately 0°;

create a tomosynthetic x-ray image reconstructed from a collection of projection x-ray images;

process the collection of the projection x-ray images in the controller into one or more reconstructed tomosynthetic x-ray images representing a volume of the specimen and relating to one or more image planes that are selectively the same or different from that of the two-dimensional x-ray image; and selectively display the two-dimensional x-ray image and the one or more reconstructed tomosynthetic x-ray images, and the method further comprises:

controlling the x-ray detector to collect projection x-ray images of the specimen when the x-ray source is energized at the selected positions such that the isocenter of the emitted x-rays at the selected positions is located at a surface of the x-ray detector, wherein one of the projection x-ray images is a two-dimensional x-ray image taken at standard imaging angle of approximately 0°;

creating a tomosynthetic x-ray image reconstructed from a collection of projection x-ray images;

processing the collection of the projection x-ray images in the controller into one or more reconstructed tomosynthetic x-ray images representing a volume of the specimen and relating to one or more image planes that are selectively the same or different from that of the two-dimensional x-ray image; and selectively displaying at least one of the one or more reconstructed tomosynthetic x-ray images on the display.

20. The method of claim 19, comprising concurrently displaying at least one of the projection x-ray images and the one or more reconstructed tomosynthetic x-ray images and presenting the electronic signals received by the gamma probe system.

* * * * *